United States Patent [19]
Klein et al.

[11] Patent Number: 5,776,141
[45] Date of Patent: Jul. 7, 1998

[54] METHOD AND APPARATUS FOR INTRALUMINAL PROSTHESIS DELIVERY

[75] Inventors: Enrique J. Klein; Aaron V. Kaplan; Mark Clifford, all of Los Altos; Martin Overbeek-Bloem, Palo Alto, all of Calif.

[73] Assignee: LocalMed, Inc., Palo Alto, Calif.

[21] Appl. No.: 704,801

[22] Filed: Aug. 26, 1996

Related U.S. Application Data

[60] Provisional application No. 60/002,847 Aug. 28, 1995.

[51] Int. Cl.$^6$ ........................................................ A61F 11/00
[52] U.S. Cl. ........................... 606/108; 606/195; 606/198
[58] Field of Search ............................... 606/108, 191, 606/192, 190, 195, 194

[56] References Cited

U.S. PATENT DOCUMENTS

| | | | |
|---|---|---|---|
| 4,292,974 | 10/1981 | Fogarty et al. | 128/344 |
| 4,323,071 | 4/1982 | Simpson et al. | 128/343 |
| 4,665,918 | 5/1987 | Garza et al. | 623/1 |
| 4,733,665 | 3/1988 | Palmaz | 128/343 |
| 4,762,129 | 8/1988 | Bonzel | 128/344 |
| 4,775,371 | 10/1988 | Mueller, Jr. | 604/280 |
| 4,776,337 | 10/1988 | Palmaz | 128/343 |
| 4,839,623 | 6/1989 | Schonstedt et al. | 336/213 |
| 4,877,030 | 10/1989 | Beck et al. | 128/343 |
| 4,950,227 | 8/1990 | Savinet Al | 606/192 |
| 5,014,089 | 5/1991 | Sakashita et al. | 355/251 |
| 5,019,090 | 5/1991 | Pinchuk | 606/194 |
| 5,026,377 | 6/1991 | Burton et al. | 606/108 |
| 5,102,417 | 4/1992 | Palmaz | 606/195 |
| 5,108,416 | 4/1992 | Ryan et al. | 606/191 |
| 5,123,917 | 6/1992 | Lee | 623/1 |
| 5,158,548 | 10/1992 | Lau et al. | 604/96 |
| 5,163,952 | 11/1992 | Froix | 623/1 |
| 5,195,984 | 3/1993 | Schatz | 606/195 |
| 5,219,355 | 6/1993 | Parodi et al. | 606/191 |
| 5,242,399 | 9/1993 | Lau et al. | 604/104 |
| 5,344,426 | 9/1994 | Lau et al. | 606/198 |
| 5,360,401 | 11/1994 | Turnland et al. | 604/96 |
| 5,360,443 | 11/1994 | Barone et al. | 623/1 |
| 5,382,261 | 1/1995 | Palmaz | 606/158 |
| 5,409,495 | 4/1995 | Osborn | 606/108 |
| 5,443,500 | 8/1995 | Sigwart | 623/1 |
| 5,445,646 | 8/1995 | Euteneuer et al. | 606/198 |
| 5,507,768 | 4/1996 | Lau et al. | 606/198 |
| 5,534,007 | 7/1996 | St. Germain et al. | 606/108 |
| 5,545,209 | 8/1996 | Roberts et al. | 623/1 |
| 5,549,563 | 8/1996 | Kronner | 606/164 |
| 5,571,086 | 11/1996 | Kaplan et al. | 604/108 |
| 5,591,222 | 1/1997 | Susawa et al. | 623/1 |
| 5,620,457 | 4/1997 | Pinchasik et al. | 606/194 |

FOREIGN PATENT DOCUMENTS

| | | |
|---|---|---|
| 0 533 960 | 3/1993 | European Pat. Off. |
| WO 95/11055 | 4/1995 | WIPO |
| WO 96/33677 | 10/1996 | WIPO |

*Primary Examiner*—Robert A. Hafer
*Assistant Examiner*—Justine R. Yu
*Attorney, Agent, or Firm*—Townsend and Townsend and Crew LLP

[57] ABSTRACT

A catheter for use in combination with a balloon angioplasty catheter for delivering stents and other intraluminal prostheses comprises a tubular catheter body having a radially expansible portion. The stent is disposed over the radially expansible portion, and structure is provided for retaining the stent on the tubular body prior to deployment. The retaining structure may be active, i.e., requiring the user to retract retaining elements, such as axial members, sheaths, or the like. Alternatively, the retaining structure may be passive, wherein balloon expansion results in release of the prosthesis from the retaining structure. Particular methods for fluoroscopically positioning stents using such delivery catheters, for delivering two or more stents using such delivery catheters, and for overexpanding the ends of the stents for anchoring them in place, are also described.

23 Claims, 22 Drawing Sheets

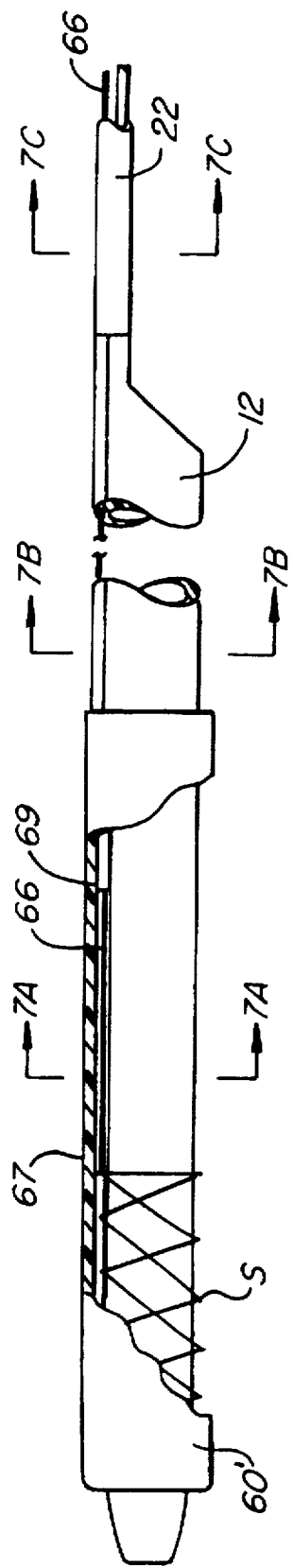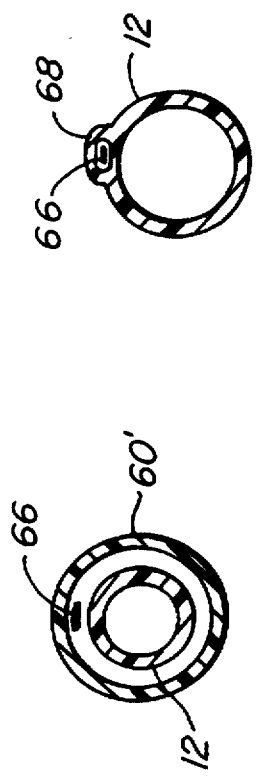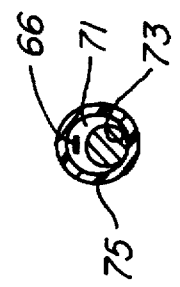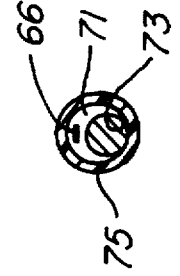

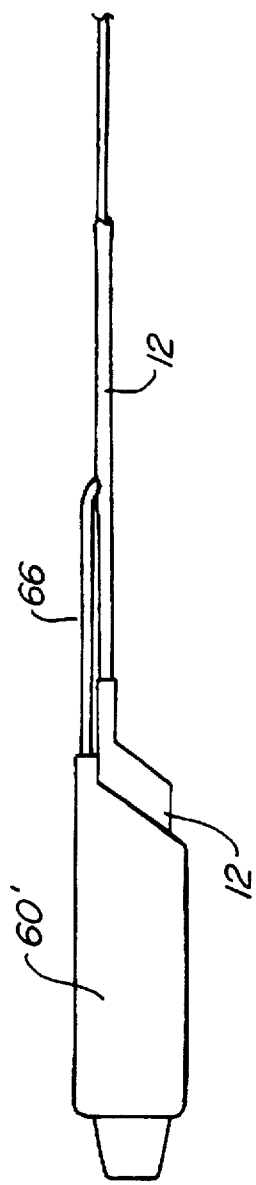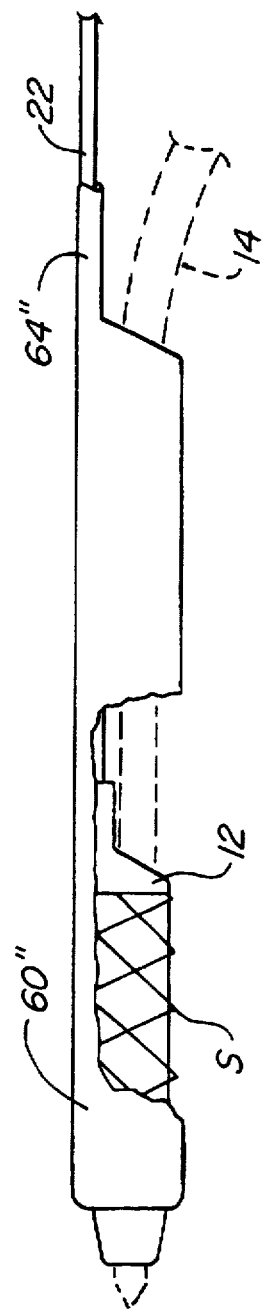

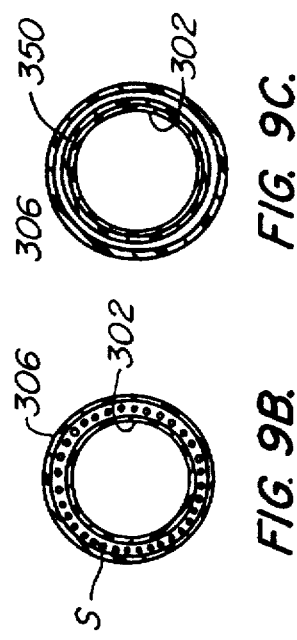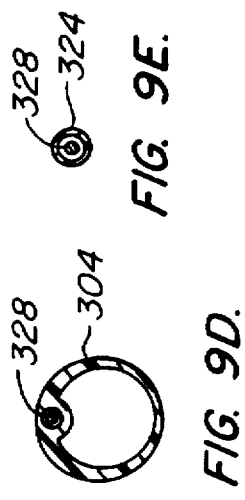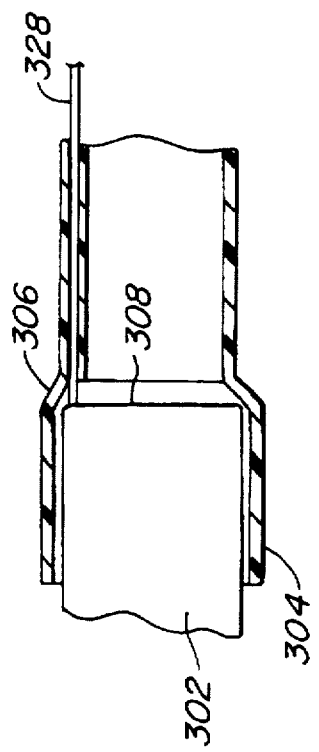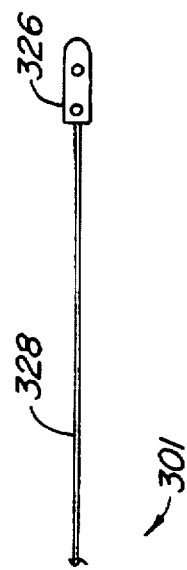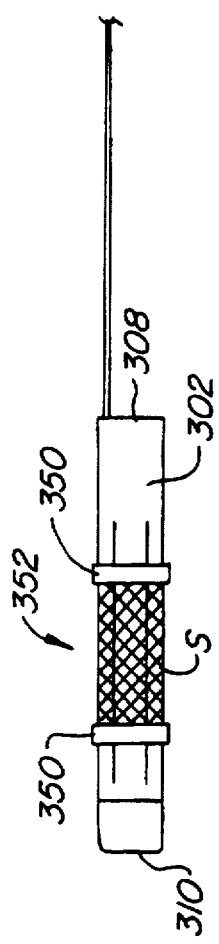

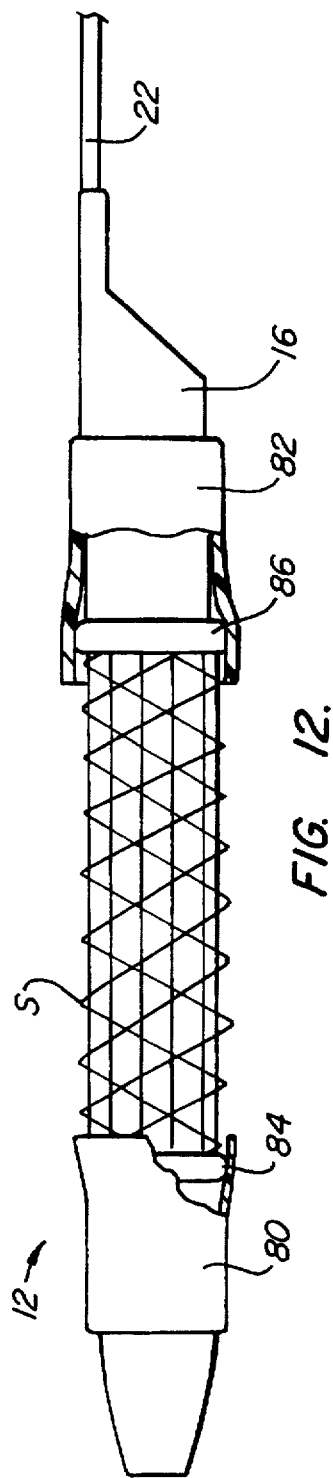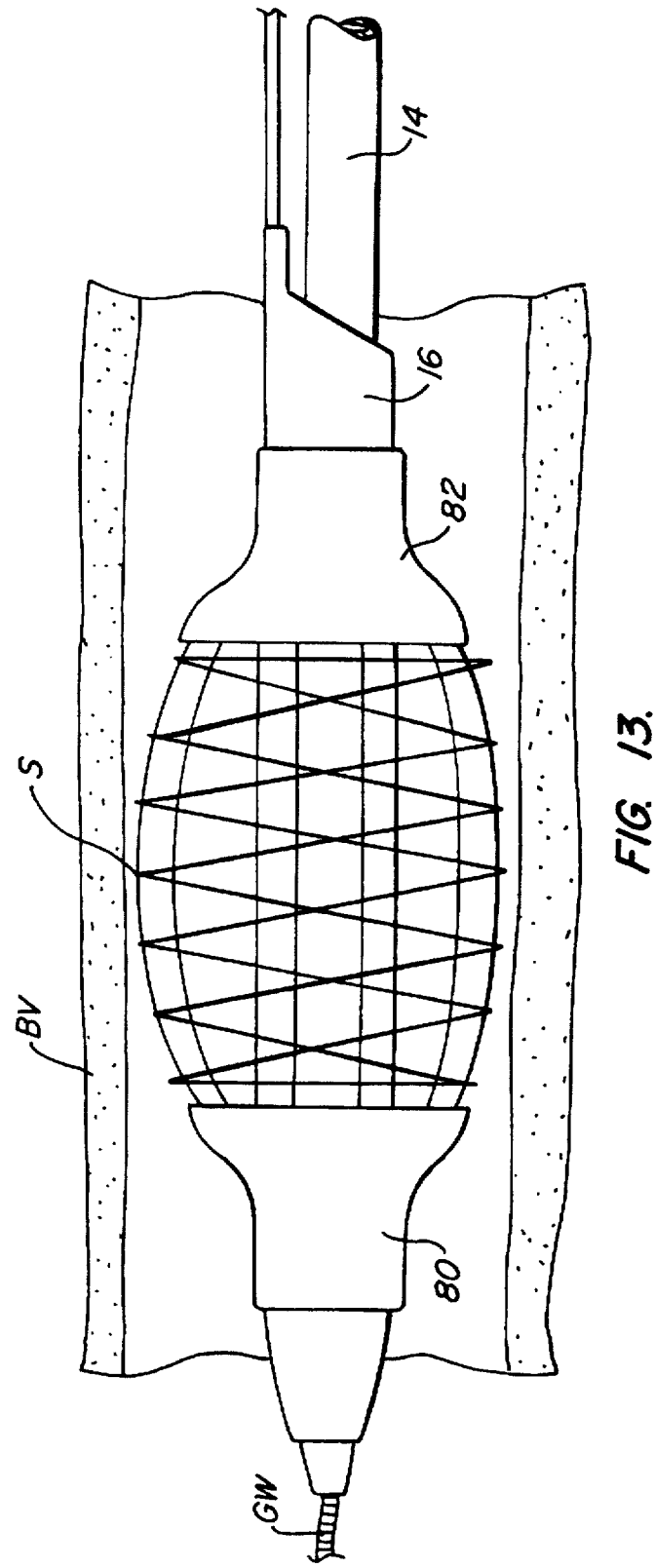

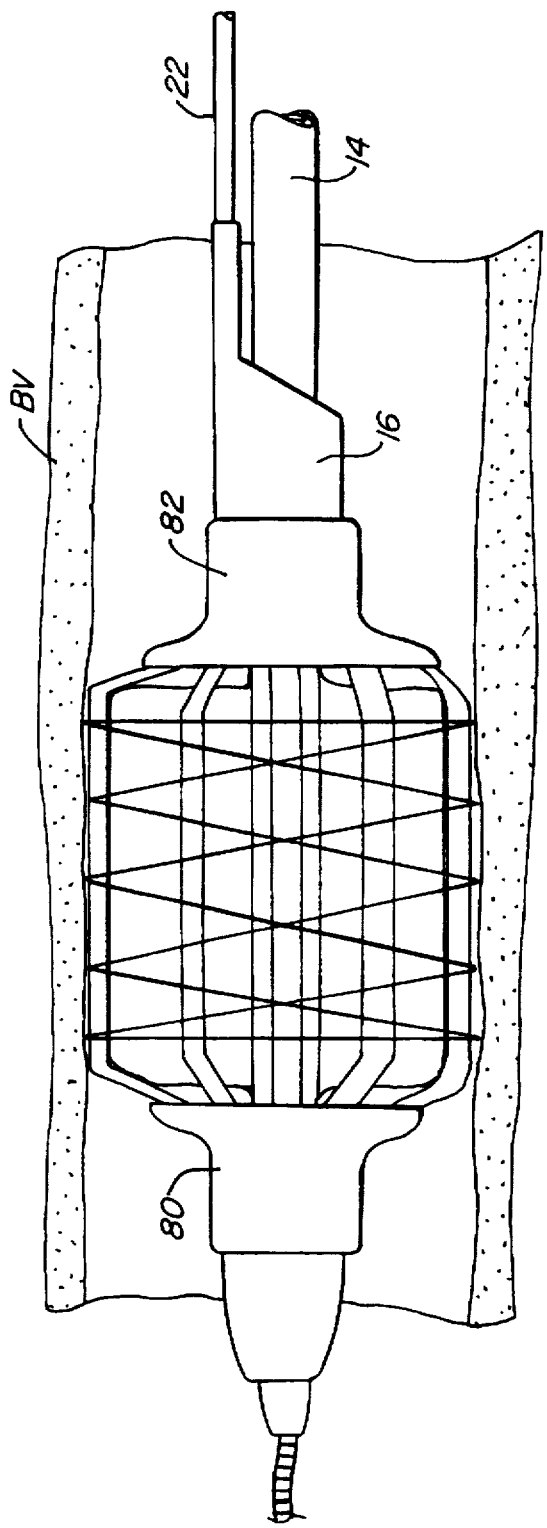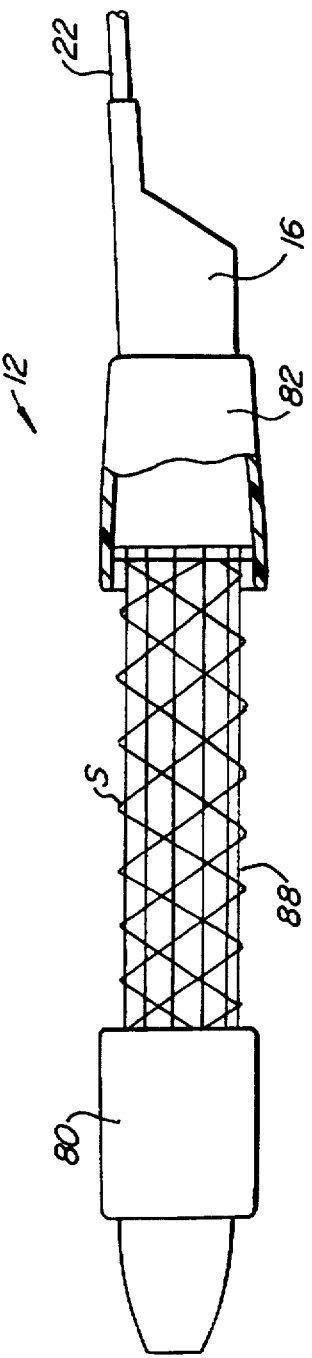
FIG. 14.
FIG. 15.

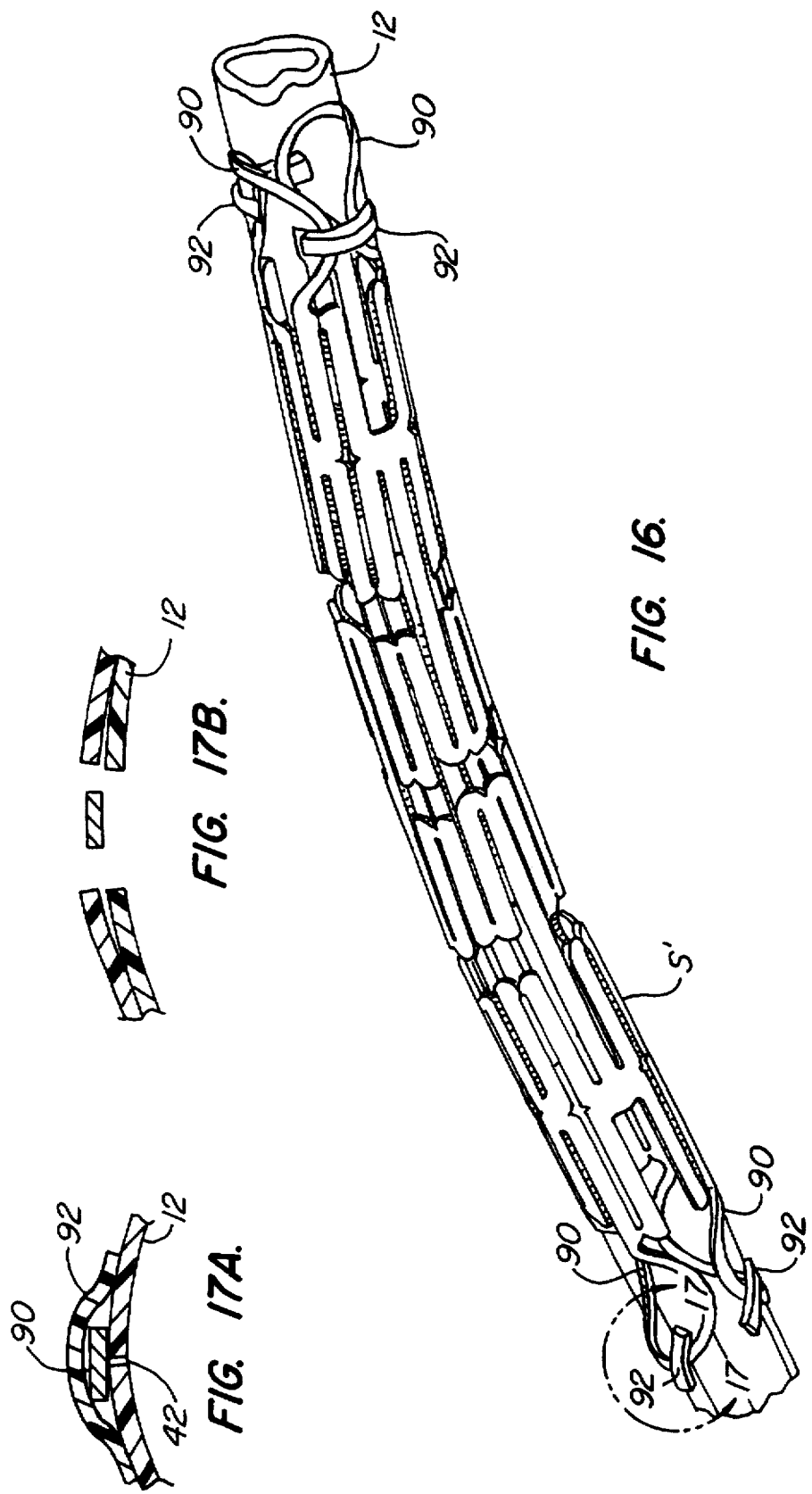

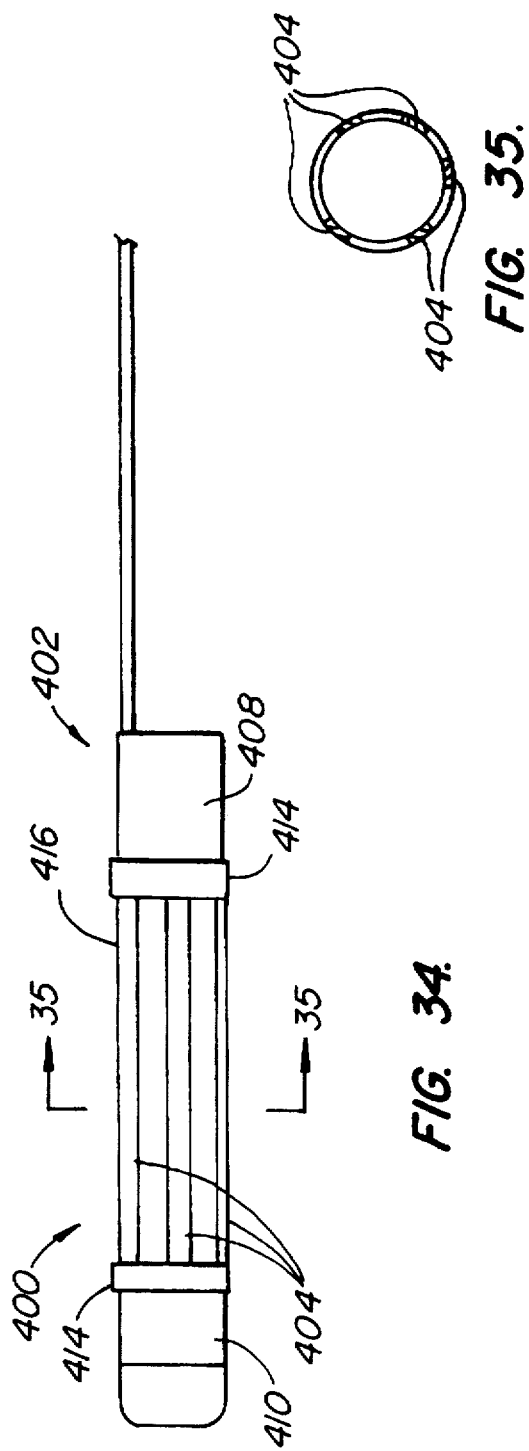
FIG. 34.
FIG. 35.
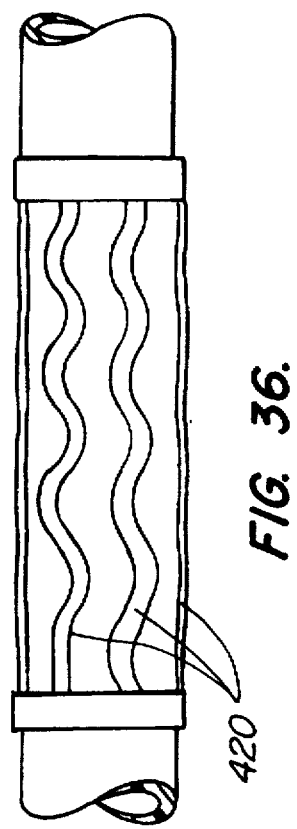
FIG. 36.

METHOD AND APPARATUS FOR INTRALUMINAL PROSTHESIS DELIVERY

CROSS-REFERENCE TO RELATED APPLICATION

This application is a continuation-in-part of provisional application Ser. No. 60/002,847, filed on Aug. 28, 1995, the complete disclosure which is incorporated herein by reference.

BACKGROUND OF THE INVENTION

1. Field of the Invention

The present invention relates generally to methods and devices for delivering tubular prostheses to intraluminal target sites. In particular, the method and device relate to the delivery of intravascular stents using a sleeve catheter to position the stent over a balloon catheter for expansion at the target site.

In percutaneous transluminal coronary angioplasty (PTCA) procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and, upon withdrawal, restores adequate blood flow through the diseased region.

While angioplasty has gained wide acceptance, it continues to be limited by two major problems, abrupt closure and restenosis. Abrupt closure refers to the acute occlusion of a vessel immediately after or within the initial hours following the dilatation procedure. This complication occurs in approximately one of twenty cases and frequently results in myocardial infarction and death if blood flow is not quickly restored. Restenosis refers to the re-narrowing of an artery after an initially successful angioplasty. Occurring usually within the initial six months after angioplasty, and restenosis afflicts approximately one in three cases. That is, approximately one in three patients will require additional revascularization procedures.

Many different strategies have been tried with different degrees of success to reduce restenosis and abrupt closure, including pharmacologic (e.g., systemic and localized administration of anti-proliferative agents and other drugs) and mechanical (e.g., prolonged balloon inflations, atherectomy, laser angioplasty, post-angioplasty thermal conditioning, and stenting). Of particular interest to the present invention, the intravascular delivery and implantation of stents to a blood vessel following balloon angioplasty procedures has proven to be of great value. The first stent to achieve widespread acceptance is the Palmaz-Schatz stent available from Johnson & Johnson Interventional Systems, a division of Ethicon, Inc., Somerville, N.J. The Palmaz-Schatz stent is a slotted tube formed from a malleable material. For delivery to the target site, the stent is provided or placed over the balloon of a balloon delivery catheter having a non-distensible balloon. The delivery catheter is then exchanged for the angioplasty balloon catheter, and the stent positioned at the angioplasty treatment site. The balloon of the delivery catheter is then inflated to expand the stent in situ in order to implant the stent within the blood vessel.

While stents have proven to be quite successful in reducing rates of restenosis and abrupt closure, prior methods and devices for delivering stents suffer from certain problems. In particular, the delivery of radially deformable stents has heretofore relied on use of a separate delivery catheter, usually in the form of a dedicated catheter which has been designed for containing and deploying the stent. The need to employ a separate balloon catheter is costly. While in some cases the angioplasty balloon catheter used to initially treat the patient is reused by manually crimping the stent thereon prior to use, the handling and positioning the stent over the deflated angioplasty balloon is difficult. Intravascular stents are very small and require significant dexterity and time in order to properly be positioned over a balloon catheter. Other concerns raised by the intravascular delivery of stents include (1) exposure of the stent on the exterior of the balloon delivery catheter which can cause trauma to the blood vessel and/or jamming within a guiding catheter during tracking, (2) loss of the stent during tracking, (3) misalignment of the stent relative to the balloon during delivery, and (4) difficulty in firmly anchoring the ends of the stent within the blood vessel following the initial balloon deployment of the stent.

For these reasons, it would be desirable to provide methods and apparatus for delivering intraluminal stents which overcome some or all of the difficulties described above. In particular, it would be desirable to provide stent delivery systems which do not require use of a separate balloon catheter for positioning and deployment of the stent. More specifically, it would be desirable to provide methods and devices which are able to reuse the balloon catheter which had been used for the primary angioplasty treatment for positioning and deployment of a stent, and in some cases two or more stents. The methods and systems of the present invention should provide for containment of the stent in the guide catheter during delivery to inhibit trauma to the vasculature and jamming of the stent and to prevent loss or misalignment of the stent from the delivery apparatus. The method and apparatus of the present invention should further inhibit deformation of the stent prior to radial expansion at the target site, and should further permit easy fluoroscopic tracking and positioning of the stent during the delivery procedure. It would be even more desirable if the methods and apparatus of the present invention could provide for improved anchoring of the ends of the stent in the blood vessel wall.

2. Description of the Background Art

The use of a tubular catheter in combination with a balloon catheter for delivering a stent to a target site in a body lumen is disclosed in copending parent application U.S. patent application Ser. No. 08/222,143, filed on Apr. 1, 1994, naming Kaplan, Kermode, and Klein as inventors, and assigned to the assignee of the present application. The full disclosure of this application has been incorporated herein by reference.

Balloon catheters specially designed for carrying and delivering stents are described in U.S. Pat. Nos. 5,507,768; 5,409,495; 5,360,401; 5,242,399; and 5,158,548; PCT published application WO 95/11055; and EP 553 960. The '768 patent describes a tubular cover that extends over the stent/balloon combination.

Sleeve catheters having a distal tubular portion adapted to receive a balloon catheter and a proximal shaft portion which will lie parallel to but not coaxially with the body of the balloon catheter are disclosed in copending application Ser. Nos. 08/461,222, filed on Jun. 5, 1995, naming Klein, Bajor, Alba, and Kaplan as inventors, and Ser. No. 08/221,613, filed on Apr. 1, 1994, naming Klein, Bajor, Alba and Kaplan as inventors, both of which are assigned to the assignee of the present application, the full disclosure of which is incorporated herein by reference.

SUMMARY OF THE INVENTION

According to the present invention, devices and methods are provided for the delivery of tubular prostheses to target locations within body lumens. While particularly intended for the post-angioplasty delivery of intravascular stents, the method would also find use with the delivery of other stents, grafts, and the like, to other body lumens, such as the delivery of urethral stents for the treatment of prostate conditions, and the like. The present invention relies on the use of a delivery catheter in combination with a separate balloon catheter, usually a conventional balloon dilatation catheter, such as a PTCA catheter. The delivery catheter of the present invention comprises a tubular catheter body having a proximal end, a distal end, a lumen therebetween, and a radially expansible portion, usually disposed near the distal end. The lumen of the catheter body is adapted to receive the balloon catheter so that the balloon of the balloon catheter can be aligned within the radially expansible portion of the catheter body. The stent, graft, or other tubular prosthesis will be positionable over the radially expansible portion of the catheter body. In this way, expansion of the balloon within the lumen of the tubular catheter body will radially enlarge the prosthesis to deploy the prosthesis within the body lumen.

The present invention provides prosthesis retaining structure on the tubular catheter body near the radially expansible portion thereof to releasably attach the prosthesis over the radially expansible portion of the body. The particular structure which is incorporated in the device can provide one or more of the design objectives described above. In particular, the structure will usually retain the prosthesis in place on the delivery catheter during the intraluminal introduction and positioning of the catheter. Thus, loss and misalignment of the prosthesis is prevented. The structure can further cover all or a portion of the prosthesis in order to reduce the risk of trauma to the body lumen and jamming of the catheter during delivery. The structure can still further inhibit unintended deformation of the prosthesis (e.g., "trumpeting" of the ends of an intravascular stent) during delivery. In addition, the structure on the catheter can be adapted to enhance fluoroscopic imaging of both the catheter and prosthesis during the delivery protocol.

The delivery catheter of the present invention preferably further comprises a proximal shaft attached to the proximal end of the tubular catheter body. The tubular catheter body will typically have a length in the range from 5 cm to 40 cm, with the radially expansible portion thereof having a length in the range from 2.5 cm to 4.5 cm. The length of the tubular body may be somewhat greater when the catheter is designed to deliver two or more stents, as described in connection with FIGS. 23–25 below. The remaining length of the delivery catheter is then provided by the proximal shaft, which has a length in the range of 90 cm to 150 cm. The proximal shaft is, typically in the form of a small-diameter metal rod or hypotube. In such an embodiment, the proximal shaft will be disposed parallel to the body of the balloon catheter within the body lumen and/or guiding catheter through which it is being delivered. In an alternative embodiment, the tubular catheter body of the delivery catheter will have a substantially greater length, typically from 100 cm to 175 cm, so that the delivery catheter may be disposed coaxially over substantially the entire length of the balloon catheter with which it is being used.

In a second particular aspect of the catheter of the present invention, the prosthesis-retaining structure is configured to axially span the entire length of the prosthesis which it is holding on the catheter body. For example, the structure may comprise a sheath which is slidable between a first position covering the radially expansible portion of the catheter body and a second position proximal to the radially expansible portion. Alternatively, the structure may comprise an evertible sheath which may be drawn down from a first position covering the radially expansible portion of the tubular catheter body and a second position which clears the expansible portion. As another alternative, the structure may comprise one or more axial members which are slidable between a position covering the expansible portion and a second position clear of the expansible portion. It will be appreciated that for each of these alternatives, the prosthesis present over the radially expansible portion of the catheter body will be contained over its entire length to prevent loss and misalignment. Moreover, in the case of the covering sheaths, the entire exterior of the prosthesis will be covered to protect against trauma and jamming during delivery. The sheaths and axial members will cover the prosthesis during the initial delivery and placement, and may then be retracted to permit radial expansion and placement of the prosthesis using the separate balloon catheter, as described in more detail below.

The prosthesis-retaining structure may alternatively be configured to engage only the proximal and distal ends of the tubular prosthesis. In particular, proximal and distal collars may be provided on the tubular body to engage and cover the proximal and distal ends of the prosthesis when the radially expansible portion of the tubular body is in its non-expanded state. When the expansible portion is radially expanded by use of the separate balloon catheter, however, the prosthesis will be radially expanded and pulled from the cover of the collars. This is particularly true of those stent designs, such as the Palmaz-Schatz stent, which axially foreshorten as they are radially expanded.

In a particular embodiment, the collars may be elastomeric and arranged to constrain expansion of the proximal and distal ends of the balloon so that the balloon expands first over its central portion. Such initial central expansion of the balloon acts to pull the ends of the prosthesis from the collars. In another embodiment, the collars may comprise serpentine rings which axially foreshorten to release the prosthesis as the tubular catheter body radially expands. In still other embodiments, the collars may be non-elastomeric (non-distensible), and will usually be split along axial lines in order to permit expansion with the tubular body.

The prosthesis retaining structure of the present invention may also comprise abutting surfaces on the tubular catheter body which engage or mate with transverse surfaces on the prosthesis, such as transverse walls or segments within or at the ends of the prosthesis. The abutting surfaces may be defined by spaced-apart rings disposed on the catheter body, and/or by the ends of a cavity formed in the catheter body. Alternatively, the abutting surfaces may be defined by protrusions ("bumps") on the catheter body which engage gaps present in the tubular prosthesis prior to radial expansion.

As yet another alternative, the retaining structure of the present invention may comprise one or more straps which secure the prosthesis to the catheter body. Straps will typically be frangible or otherwise constructed or attached so that the straps will release the prosthesis in response to radial expansion of the catheter body.

The radially expansible portion of the tubular catheter body may be formed in a variety of ways. For example, it may be defined by forming a plurality of axial slits in the tubular wall of the catheter body. The slits move circumferentially apart as the tubular body is radially expanded by inflation of a balloon therein. Alternatively, the expansible portion may be formed by fabricating the tubular body at least in part from an elastomeric material which permits expansion. In another preferred embodiment, an axially split tubular catheter body is modified by the inclusion of non-distensible or elastomeric webs between adjacent axial segments. The axial segments resulting from splitting of the tubular body provide significant column strength, while the web portions fully contain the balloon within the lumen of the catheter body even after full expansion. The use of non-distensible webs can further be relied on to limit maximum balloon expansion, if so desired.

The delivery catheter of the present invention is preferably combined with a radially expansible tubular prosthesis which is disposed over the radially expansible portion of the tubular catheter body. Such "pre-loading" of the stent or other prosthesis eliminates the need for the placement of the stent over the delivery system at the time of use. The delivery catheters of the present invention, moreover, are significantly less expensive than the use of a separate balloon delivery catheter. Preferably, the pre-loaded delivery catheters of the present invention will be present in a sterile package so that they are immediately available for use with minimal additional preparation.

According to the methods of the present invention, a tubular catheter body having the prosthesis disposed over a radially expansible portion thereof is positioned over a balloon catheter at a target site within a body lumen. The balloon catheter is expanded within the lumen of the tubular catheter to expand the prosthesis in situ at the target site. Prior to or during expansion, the prosthesis will be released from the tubular catheter body. The releasing step typically comprises selectively releasing a constraint on the prosthesis prior to inflating the balloon. For example, the constraint releasing step may comprise drawing a sheath from over the prosthesis, drawing one or more axial members from over the sheath, or other such active steps. Alternatively, the releasing step may be responsive to the balloon inflation step. For example, the releasing step may comprise shortening of the prosthesis as a result of radial expansion of the tubular catheter body. In such a case, the prosthesis may be released from a pair of spaced apart collars, as described above. Alternatively, the collars themselves may axially foreshorten upon radial expansion of the tubular catheter body, as in the case of elastic serpentine rings described in more detail below. As a further alternative, the releasing step may comprise breaking a strap or other engaging members as a result of radial expansion of the tubular body, also as described above.

In another aspect of the present invention, a radially expansible tubular prosthesis is delivered to a target site under fluoroscopic imaging. A tubular catheter body carries the tubular prosthesis over a radially expansible portion thereof. A fluoroscopic marker on the tubular catheter body is aligned with a fluoroscopic marker on a balloon catheter so that the tubular prosthesis is properly aligned over the radially expansible portion of the catheter body. A pair or axially spaced apart fluoroscopic markers, either on the prosthesis or on the catheter body, are then verify positioning of the prosthesis within the target site and/or to position the prosthesis prior to delivery by moving the balloon catheter and tubular catheter body in unison.

In another specific aspect of the method of the present invention, two or more radially expansible tubular prostheses may be delivered to the same or different target sites in a body lumen. At least two tubular prostheses are carried on a tubular catheter body which has axially spaced-apart radially expansible portions. A first of the radially expansible portions having a prosthesis thereover (usually the distalmost) is then positioned at a first location within the body lumen. The prosthesis may be delivered by expanding a balloon therein, generally as described above. A second radially expansible portion of the tubular body, also carrying a prosthesis, is then positioned at a second target site within the body lumen. The same balloon is then inflated within the tubular catheter body to deploy the prosthesis at the second target site.

In yet another aspect of the method of the present invention, a deployed tubular prosthesis in a body lumen may be anchored by positioning a tubular catheter over a balloon within the deployed prosthesis. The balloon is then inflated within the tubular catheter to expand the catheter and engage at least one protrusion on the catheter body against the end of the prosthesis to selectively expand and anchor said end within the lumen. Preferably, the tubular body will include a pair of spaced-apart protrusions, so that a single expansion of the balloon will engage both protrusions against the two ends of the prosthesis.

BRIEF DESCRIPTION OF THE DRAWINGS

FIGS. 7, 7A, 7B, and 7C illustrate a preferred embodiment of the retaining structure of FIG. 6.

FIG. 8 illustrates an additional variation of the embodiment of FIG. 6.

FIG. 9 illustrates a further variation on the embodiment of FIG. 6.

FIGS. 9A–9H illustrate a specific embodiment of a prosthesis delivery catheter having the features of the catheter of FIG. 9.

FIGS. 12–14 illustrate a fourth exemplary embodiment of the retaining structure of the present invention, wherein a pair of axially spaced-apart collars constrain opposite ends of the tubular prosthesis on the deliver catheter of the present invention prior to balloon deployment.

FIG. 15 illustrates a fifth exemplary embodiment of a prosthesis delivery catheter according to the present invention, wherein a prosthesis is retained within a cavity on the tubular catheter body and wherein a pair of spaced-apart collars overlap opposite ends of the cavity.

FIG. 16 illustrates a sixth exemplary embodiment of the retaining structure of the present invention, wherein a plurality of individual straps anchor a prosthesis to the catheter body.

FIGS. 17A and 17B illustrate the release of a structural element of the prosthesis of FIG. 16 from the strap.

FIGS. 34–36 illustrate alternative embodiments for the radially expansible portion of the delivery catheters of the present invention.

DESCRIPTION OF THE SPECIFIC EMBODIMENTS

Figure 1:
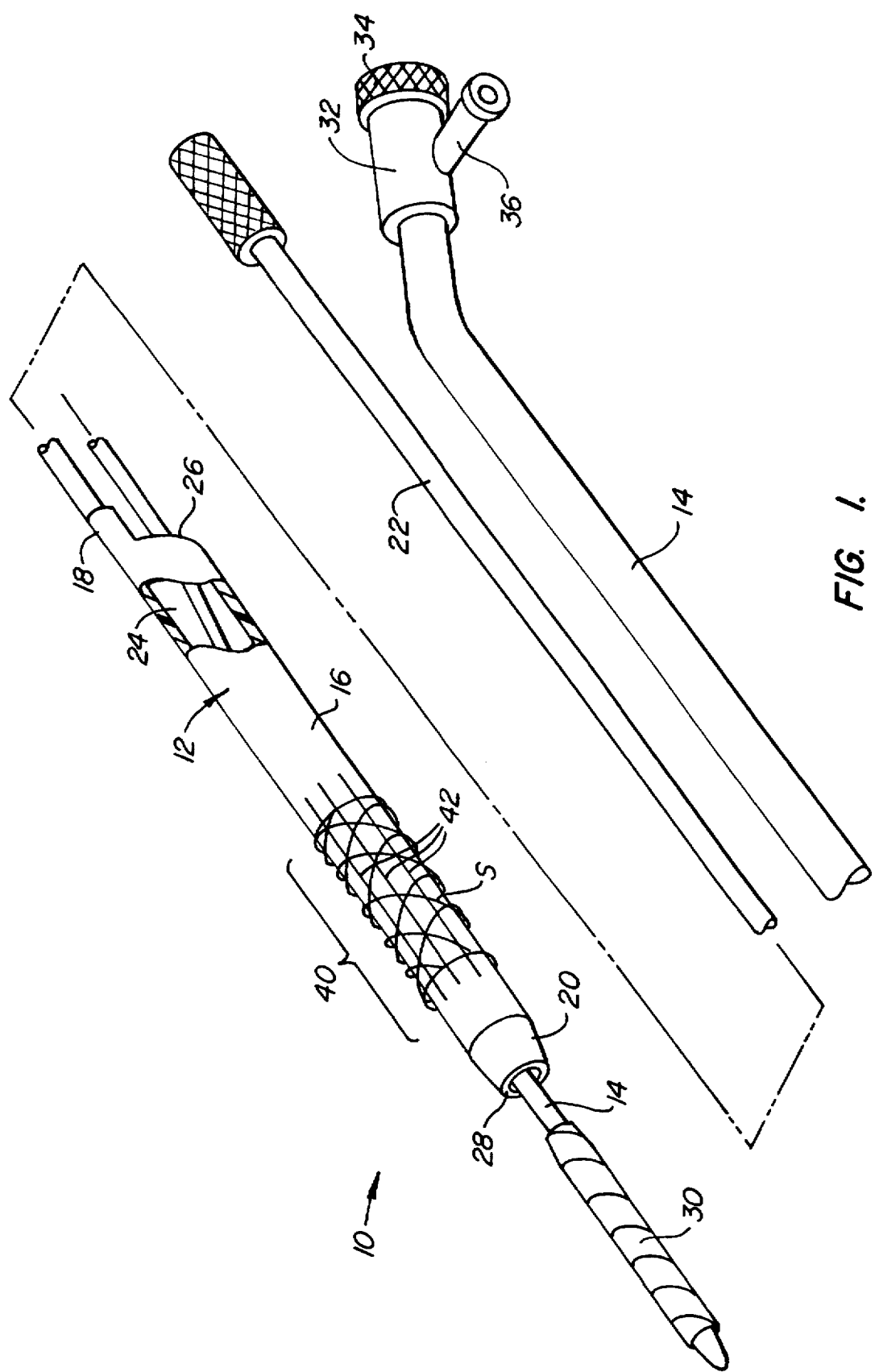
FIG. 1 is a perspective view of a prosthesis delivery catheter constructed in accordance with the principles of the present invention, with specific prosthesis retaining structures shown in FIGS. 2–16.
Figure 2:
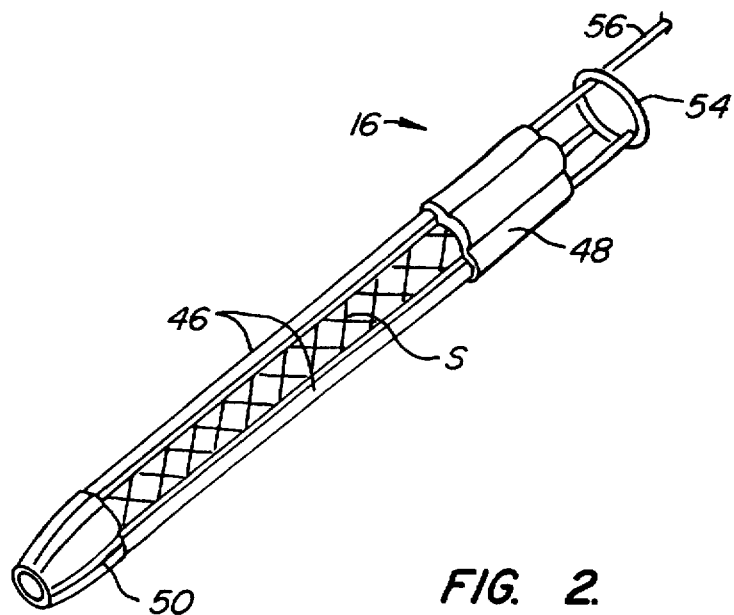
FIGS. 2–5 illustrate a first exemplary retaining structure employing a plurality of retractable axial members which cover the prosthesis prior to balloon deployment.
Figure 3:
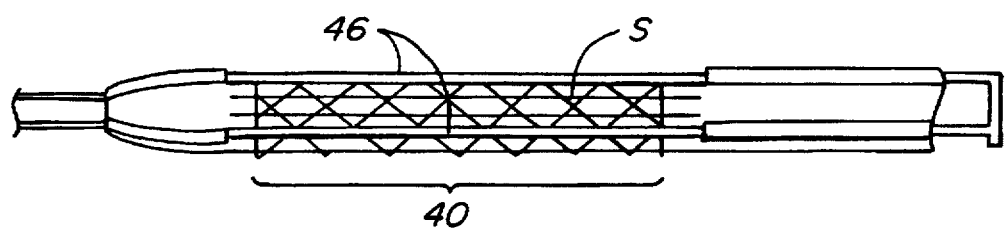

The present invention provides methods and devices for performing multiple, sequential intraluminal procedures on a patient as part of a therapeutic treatment. By "intraluminal," it is meant that the procedures occur at a target site within a body lumen, usually being within the patient vasculature, more usually being within the arterial system, including the coronary arteries, the peripheral arteries, and the cerebral arteries. The methods and devices of the present invention, however, are not limited to use in the vascular system, and may also be advantageously employed in other body structures, including the prostate via the prostatic urethra, (e.g., to treat benign prostatic hypertrophy (BPH), or adenocarcinoma), the fallopian tube via its lumen (to treat strictures), brain parenchyma (to treat Parkinson's disease), and the like.

The "target site" within the body lumen will usually be diseased or be suspected of being diseased. In the case of vascular treatment, the target locations will usually be stenotic regions which have previously been treated conventional balloon angioplasty procedures using a balloon angioplasty catheter which may be reused in the method of the present invention, as described below.

The apparatus and methods of the present invention are particularly intended for the delivery of tubular prostheses to the target site in the body lumen. Tubular prostheses include both stents and graft structures, particularly intravascular stents and grafts of the type used to maintain vessel patency following balloon angioplasty treatment procedures. The stent and graft structures are preferably of the malleable or deformable type wherein the stent is initially in a narrow diameter configuration to facilitate intraluminal delivery. After placement at the target site, the stent or graft is expanded in situ by internal inflation of a balloon, causing plastic deformation of at least a portion of the stent or graft structure in order to maintain radial expansion after the balloon is removed. Such malleable and deformable prosthesis are well-described in the patent and medical literature. See, for example, U.S. Pat. Nos. 4,733,665; 4,776,377; 4,839,623 (a prostatic stent); 4,877,030; 5,019,090; 5,102, 417; 5,123,917; 5,163,952 (a polymeric graft which is expanded by internal balloon inflation); 5,195,984; 5,219, 355; 5,344,426; 5,360,443; and 5,382,261, the full disclosures of which are incorporated herein by reference.

The present invention provides a delivery catheter intended for use in the intraluminal introduction and positioning of a tubular prosthesis at the target site. The delivery catheter will be used in combination with a balloon catheter for expanding the tubular prosthesis, where in the case of intravascular treatment, the balloon catheter is typically an angioplasty catheter of the type described in U.S. Pat. Nos. 5,014,089; 4,762,129; 4,775,371; 4,323,071; and 4,292,974, the full disclosures of which are incorporated herein by reference. Such balloon angioplasty catheters are commercially available from a number of vendors, such as Advanced Cardiovascular Systems, Inc., Sunnyvale, Calif.; C. R. Bard, Murray Hill, N.J.; Medtronic, Inc., Minneapolis, Minn.; and others.

The delivery catheter of the present invention will comprise a tubular catheter body having a proximal end, a distal end and a lumen therebetween. At least a portion of the wall of the tubular catheter body will be radially expansible to permit expansion of the balloon catheter therein. The radially expansible portion will typically have a length in the range from 2.5 cm to 4.5 cm and may be provided by a variety of specific designs which permit both placement of the prosthesis thereover and internal inflation of the balloon catheter to permit radial expansion of the prosthesis. Preferably, the tubular catheter will have a relatively thin wall, but will have sufficient column strength to permit positioning of the catheter body over the balloon catheter, as described in more detail hereinafter.

The lumen of the tubular catheter body will be sized to receive the balloon of the balloon catheter, typically after the balloon has been inflated once to effect the initial angioplasty treatment. Since the balloon seldom folds down to its original profile, the lumen diameter of the tubular catheter body will have to be sized slightly larger than would otherwise be the case. Typically, the lumen diameter of the tubular catheter body will be in the range from 1.0 mm to 1.5 mm, preferably from 1.0 mm to 1.3 mm. Typically, specific lumen diameters will be provided to correspond to differently sized balloon angioplasty catheters. Thus, the treating physician will have a number of delivery catheters with pre-loaded stents according to the present invention available, where the physician can choose one size specifically based on the size of the artery and of the angioplasty balloon which has been used for primary treatment of the stenosis.

The tubular catheter body may have a length sufficient to receive the entire balloon catheter, typically have a length in the range from 100 cm to 175 cm, preferably from 110 cm to 150 cm. Usually, however, the tubular catheter body will not extend the entire length of the balloon angioplasty catheter, but will instead have a length in the range from 5 cm to 40 cm, preferably from 8 cm to 30 cm. The length will be sufficient to at least cover the entire length of the balloon on the balloon angioplasty catheter, and will often have a length sufficient to extend from the distal end of the balloon angioplasty catheter through the coronary vasculature into the guiding catheter which is used to place the angioplasty balloon catheter. In such cases where the tubular catheter body does not extend the entire length of the balloon catheter, the delivery catheter will further comprise a proximal shaft attached to the proximal end of the tubular catheter body. The proximal shaft can consist essentially of a small diameter rod or tube, with an outside diameter typically in the range from 0.3 mm to 0.8 mm, and which has sufficient flexibility to be introduced through relatively non-tortuous regions of the vasculature but which has sufficient column strength to allow axial translation of the tubular catheter body through more tortuous regions of the vasculature. For example, stainless steel wire could be used, covered with a polymeric sleeve with sufficient annular space between the sleeve and the wire to accommodate one ore more pull wires. Alternatively, a stainless steel hypotube can be used, wherein the lumen of the hypotube can provide access for pullwires or other elements used to retract the protective structure of the present invention, as described in more detail below.

Referring now to FIG. 1, a catheter system 10 comprising a prosthesis delivery catheter 12 constructed in accordance with the principles of the present invention and a conventional balloon catheter 14 is illustrated. The prosthesis delivery catheter 12 comprises a tubular catheter body 16 having a proximal end 18 and a distal end 20. A proximal shaft 22 is attached to the proximal end 18 of the tubular catheter body 16. Tubular catheter body 16 includes an internal lumen 24 which extends from proximal port 26 to a distal port 28 to receive the balloon catheter 14. In particular, the lumen 24 will be sized sufficiently large to receive the balloon 30 of balloon catheter 14, which will typically be only partially refolded after an initial deployment in an angioplasty procedure. The balloon catheter 14 further includes a proximal Y-connector 32 including an axial connector 34 for receiving a guidewire and a branch connector 36 for attachment of a balloon inflation device.

The tubular catheter body 16 includes a portion 40 which is radially expansible. As illustrated, the radially expansible portion 40 is defined by a plurality of axial slits 42 which permit axial segments therebetween to circumferentially spread apart as the balloon 30 is expanded therein. A stent S is mounted over the exterior of the tubular catheter body and axially aligned with the radially expansible portion 40 thereof so that the stent may be expanded by balloon inflation. For simplicity, the stent S is illustrated as a pair of counterwound helices. The structure of the stent, of course, can be any conventional stent or graft structure which is expanded by the application of internal pressure such as by inflation of a balloon catheter therein.

Figure 4:
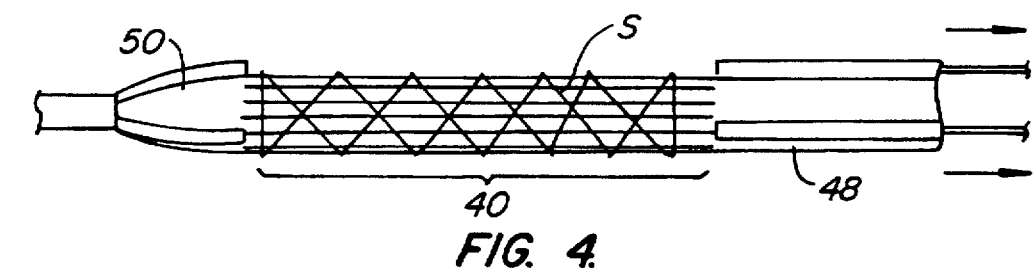
Figure 5:
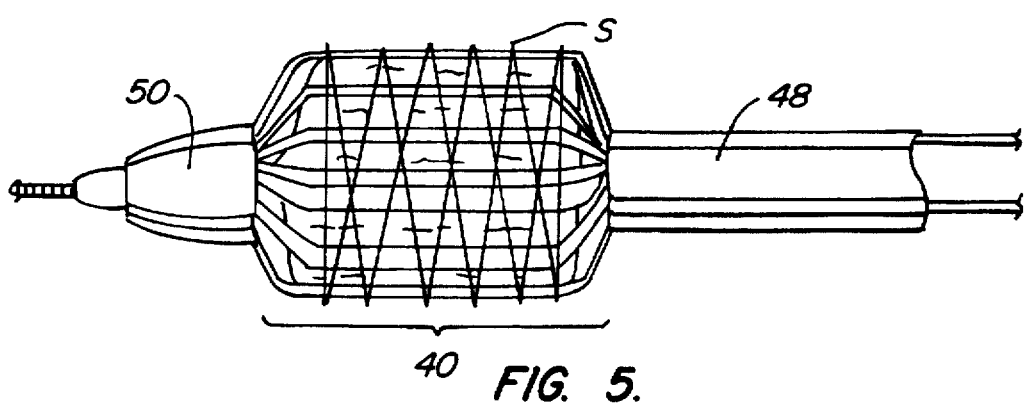

The tubular catheter body 16 can be modified in a number of ways in order to provide the prosthesis retaining structure of the present invention. The first such structure is illustrated in FIGS. 2–5, wherein three axially retractable members 46 are shown extending over the stent S. The axial members 46 initially extend from a proximal retainer 48 to a distal retainer 50. The proximal retainer includes a plurality of lumens which permit relative movement of the axial members 46 therein. The distal retainer includes lumens or cavities for receiving the distal ends of the axial members 46. A mechanism is provided for simultaneously withdrawing the three axial members 46 prior to deployment of the stent S. For example, the axial members 46 may be coupled together by a ring 54 and a pullwire 56 provided through the lumen of or adjacent to proximal shaft 22 to permit the user to selectively retract the axial members at an appropriate time in the procedure. Shown in FIGS. 2 and 3, stent S is covered by the axial members 46. After positioning the angioplasty balloon and the stent S at the target site, the axial members 46 may be proximally withdrawn, as illustrated in FIG. 4. A balloon 30 on the balloon catheter 14 may then be expanded within the radially expansible portion of the tubular catheter body, expanding the stent S as shown in FIG. 5.

Figure 6:
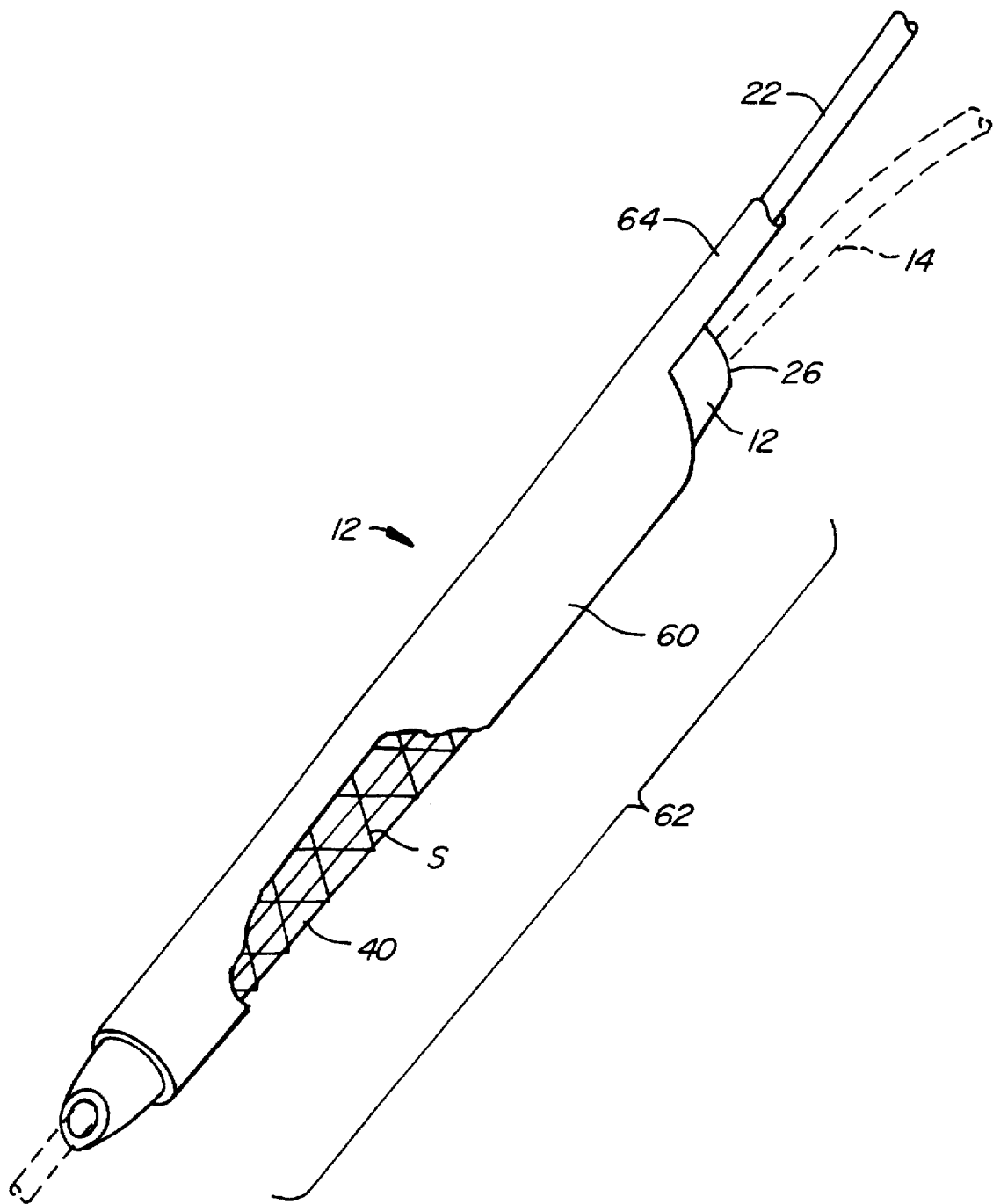
FIG. 6 illustrates a second exemplary embodiment of the retaining structure which employs a retractable sheath which covers the prosthesis prior to balloon deployment.

An embodiment of the catheter 12 having a retractable sheath 60 disposed over the radially expansive section 40 of the tubular catheter body as well as over the stent S, is illustrated in FIG. 6. The sheath 60 includes a large diameter portion 62 which is received over the tubular catheter body 12 and a narrow diameter portion 64 which is received over the proximal shaft 22. Thus, access to the proximal port 26 is not impeded by the sheath, so the balloon catheter 14 may be introduced while the sheath remains covering the stent S. Prior to deployment of the stent S, however, the sheath 16 may be retracted by drawing axially on the narrow diameter portion 64. The narrow diameter portion 64 could extend proximally the remaining length of the shaft 22. Alternatively, the section 64 could be coupled to a pullwire or other mechanism located adjacent to or within a lumen of shaft 22. A variety of specific designs for retraction of the sheath are available.

As shown in FIG. 6, both the tubular body 12 and the sheath 60 are relatively long. In particular, their lengths will be sufficient to extend from a treatment site within the coronary arteries back into a guiding catheter adjacent the coronary os, typically having a length from about 15 cm to 25 cm. In this way, the entry port 26 will remain within the guiding catheter at all times. Relative movement of the proximal port 26 of the delivery catheter 12 will largely be limited to within the protection of the guiding catheter.

A particular embodiment of catheter 12 with a sheath 60' is illustrated in FIGS. 7, 7A, 7B, and 7C. A pull wire 66 is connected to the sheath 60' at a center location immediately proximal to the proximal end of stent S. The pull wire 66 extends into a wire lumen 68 which is formed integrally with the tubular catheter body 12. The wire lumen 68 terminates at distal end 69 which is protected within the sheath 60' during introduction of the catheter. In this way, the pull wire 66 can be withdrawn proximally to retract the sheath 60' and expose the stent S while the wire is fully protected by the sheath. The wire 66 may extend through the hollow lumen of a hypotube used as shaft 22. Alternatively, and preferably, the wire 66 extends through an annular lumen 71 formed between a solid core rod 73 and an exterior cover 75, as best illustrated in FIG. 7C.

An embodiment of the delivery catheter of the present invention having a short sheath 60' and a short tubular catheter body 12 is illustrated in FIG. 8. Yet another embodiment of the delivery catheter, this time having a short tubular catheter body 12 and a long protective sheath 60" is illustrated in FIG. 9. Each of these embodiments may find use under particular circumstances.

Figure 9A:
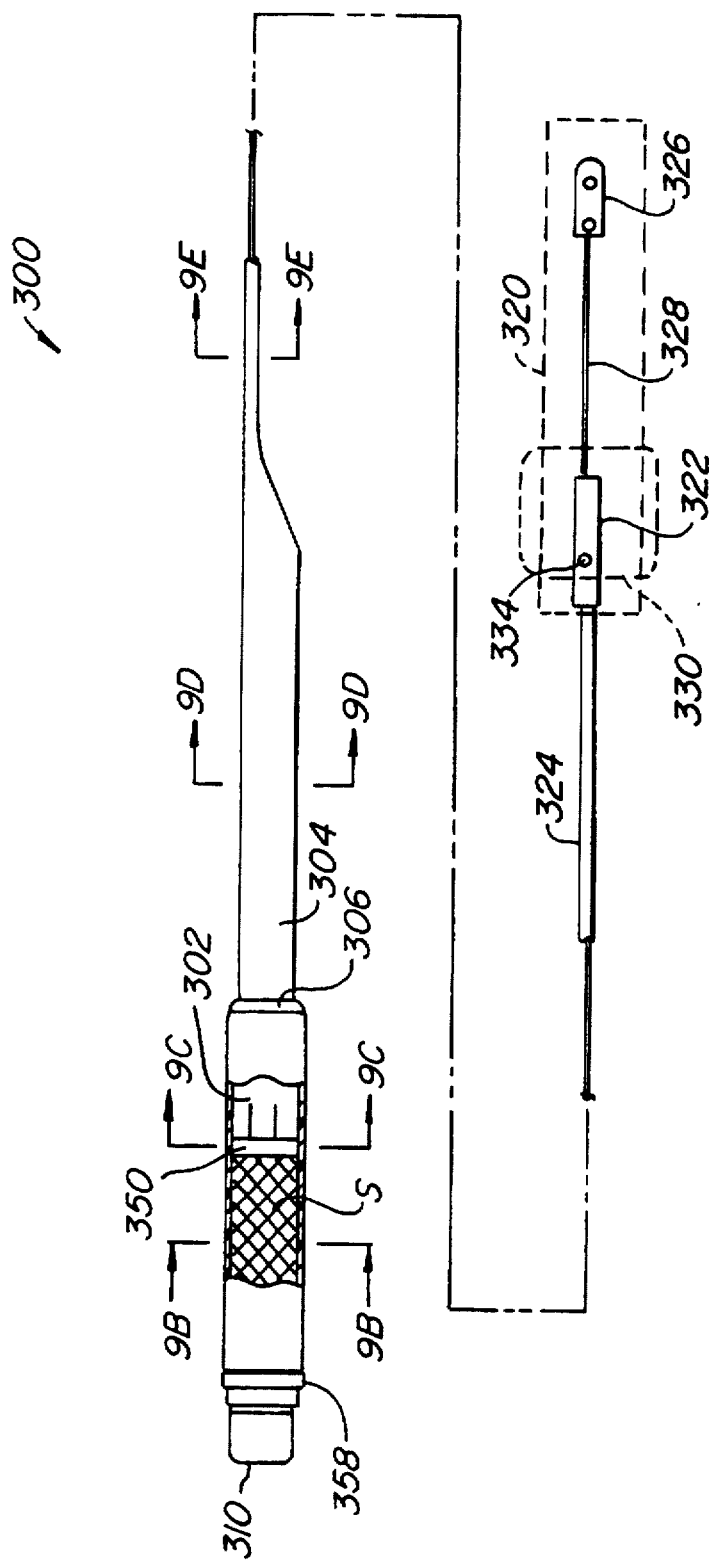

A delivery catheter system 300 including a delivery catheter 301 (FIG. 9G) having a short tubular body 302 and a long sheath 304 as illustrated in FIGS. 9A–9H. The catheter system 300 incorporates a number of features intended to facilitate retraction of the sheath 304 from over the stent S which is carried on the short tubular body 302 of catheter 301 as well as to enhance containment of the stent within the sheath. A first of these features comprises a shoulder 306 formed in the sheath 304, where the shoulder engages a proximal end 308 of the short sleeve 302 of the delivery catheter to prevent the sheath from accidently extending beyond the distal end 310 of the delivery catheter (FIG. 9F).

Figure 9H:
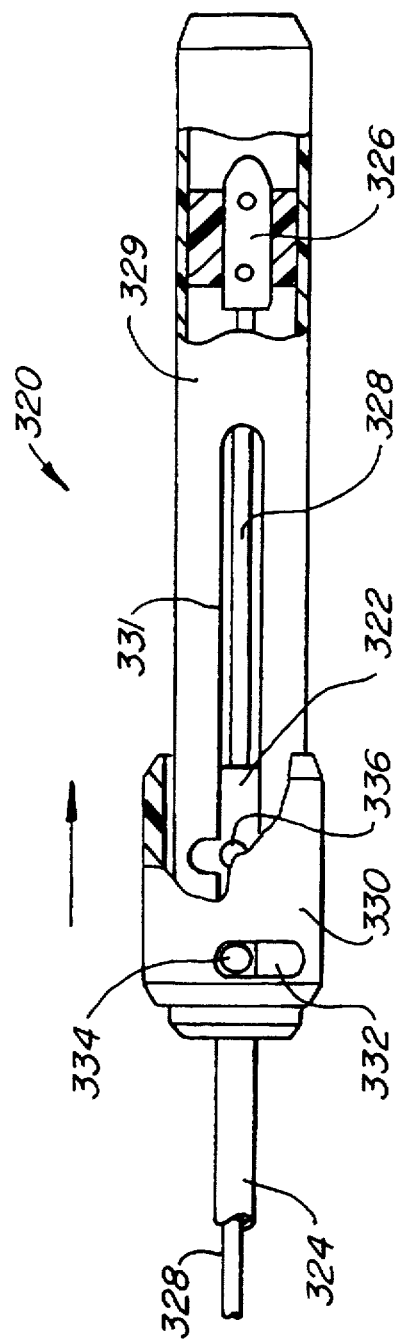

The second feature comprises a handle 320 (FIGS. 9A and 9H) which controls relative axial motion between a first proximal anchor 322 at the proximal end of sheath extension 324 and a second proximal anchor 326 at the proximal end of rod 328. The handle 320 comprises a tubular body 329 and a locking collar 330 having a slot 332 which engages a pin 334 fixed to the first proximal anchor 322. A second pin 336 is attached to the inner surface of the collar 330 and travels in an T-shaped slot 331 on the tubular body 329. The collar 330 may thus be twisted to align pin 336 in the axial segment of slot 331 so that the collar may be proximally retracted to withdraw pin 334 (which is constrained in slot 332) and sheath extension 324 (and thus the entire sheath 304) proximally relative to the short sleeve 302 of the delivery catheter. The delivery catheter sheath 304 and sheath extension 324 are immobilized relative to the short sleeve 302 by means of handle 320. FIG. 9H shows the collar 330 unlocked and ready to be proximally retracted to uncover the sheath 304 from the short tubular body 302. The handle 320 may also be provided with locking detents (not shown) at both ends of the travel of collar 330 relative to the tubular body 329.

An additional feature of delivery catheter 301 comprises radiopaque marker rings 350 which define location 352 which receives the stent therebetween. The marker rings 350 will be raised slightly from the exterior surface of the sleeve 302 so that they form a cavity or receptacle for the stent S. The rings 350 will be formed so that they can expand together with the sleeve 302 as a balloon catheter is expanded therein (illustrated hereinafter). Preferably, the radiopaque markers are formed from a polymeric material, such as a polyether block amide (e.g. Pebax, available from Elf Atochem, Philadelphia Pa.) loaded with from 80% to 90% of tungsten particles. Such polymeric radiopaque rings can be thermally bonded to the sleeve 302 and can be axially cut so that they can expand together with expansion of the sleeve. The material is also highly radiopaque.

The extension 324 of the sheath 304 may be formed integrally with the sheath, but will preferably be formed from a different material having a very high tensile strength and low elongation characteristic. While the large diameter portion of the sheath 304 may be formed from a PTFE or polyethylene, the extension 324 will typically be formed from a polyimide, reinforced polyimide, or polyether ether ketone (PEEK). The sheath 304 will also have a radiopaque marker 358 which may be a conventional radiopaque marker, or be composed of the tungsten-loaded polymer described above. The rod 328 of the delivery catheter may be a solid core rod, hypotube, or other material, generally as described above with the previous embodiments.

In a preferred design of the catheter system 300, the distal end 310 of the delivery catheter 301 will be soft and expansible in order to accommodate relatively large balloon catheters (when the balloon is uninflated). The ability to pass the balloon through the distal end 310 of the delivery catheter 301 allows for a predilation of the stent prior to its full dilation through balloon expansion, as will be described in greater detail in connection with FIGS. 28-33 below.

Figure 10:
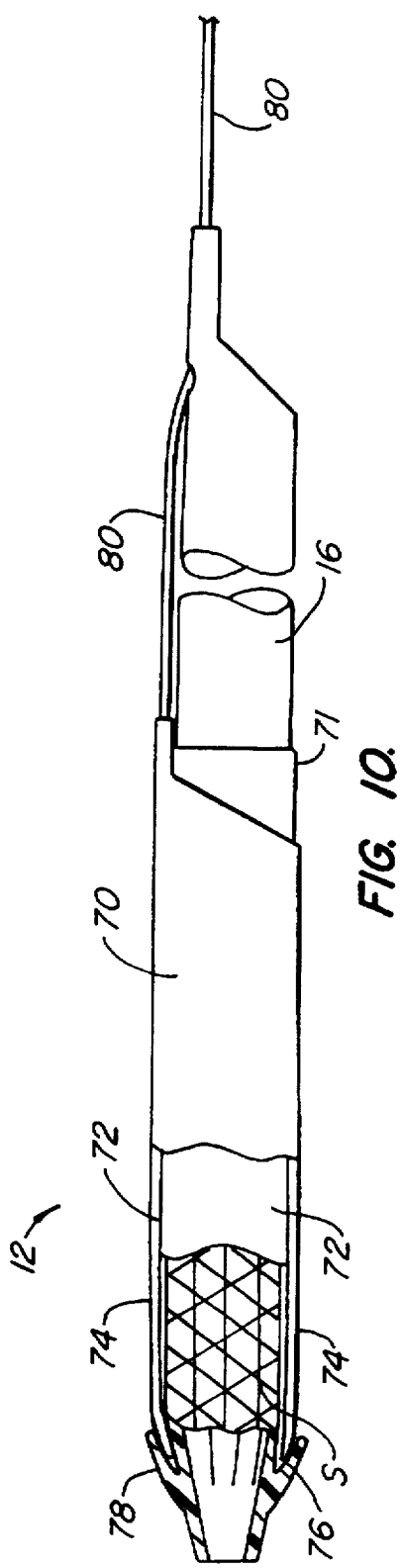
FIGS. 10–11 illustrate a third exemplary embodiment of the retaining structure of the present invention, employing an evertible sheath for covering a prosthesis prior to balloon deployment.
Figure 11:
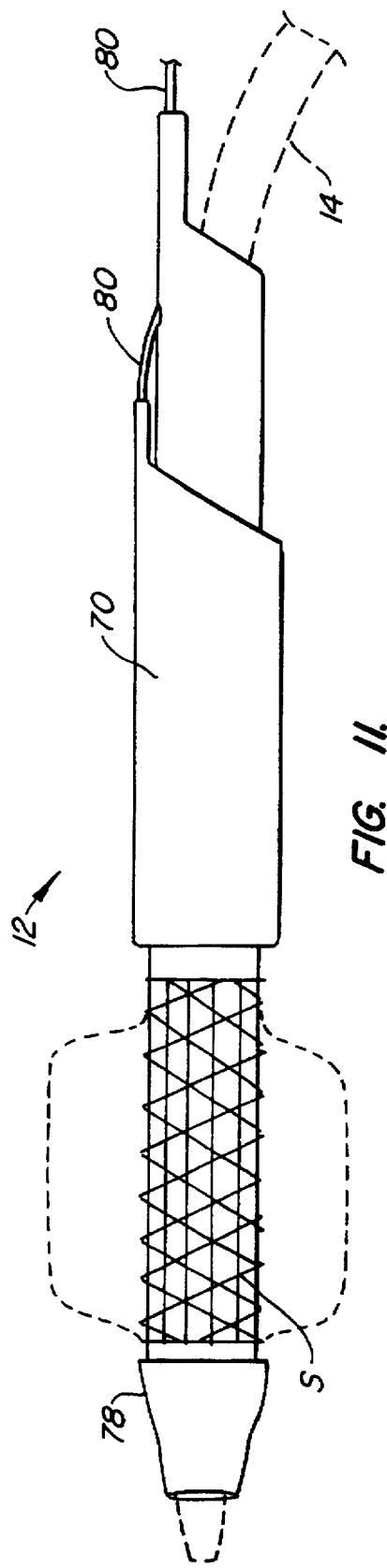

A delivery catheter 12 employing an evertible sheath 70 as the stent retaining structure is illustrated in FIGS. 10 and 11. The evertible sheath 70 is attached to the catheter body 16 at location 71 folded over into an inner layer 72 and an outer layer 74. Initially, a distal fold 76 on the sheath 70 is constrained within an annular retainer 78 which radially constrains the end over distal end of the catheter body and the stent S. A pullwire 80 is attached to the proximal end of the outer layer 74 of the sheath 70. In this way, the pullwire 80 may be proximally withdrawn to pull back the sheath 70, as illustrated in FIG. 11. After the stent S has been uncovered, it may be deployed by the internal balloon catheter 14 as described previously and illustrated in broken line in FIG. 11.

Referring now to FIGS. 12-14, a prosthesis delivery catheter 12 comprises tubular catheter body 16, generally as set forth above. Structure for retaining the stent S comprises axially spaced-apart collars 80 and 82 and axially spaced-apart rings 84 and 86. The rings 84 and 86 provide axial constraint by abutting against the proximal and distal end of the stent S. The collars 80 and 82 provide radial constraint on each end of the stent S. Such structure both holds the stent S in place and covers each end of the stent S, preventing these ends from deforming and traumatizing the vascular wall. An advantage of the prosthesis retaining structure of FIGS. 12-14 is that the stent S is automatically released in response to balloon inflation. That is, there is no need to provide a separate step for releasing the stent S prior to balloon expansion. Preferably, the collars 80 and 82 are elastomeric so that they partially constrain the internal expansion of the balloon during the initial stages of expansion, as illustrated in FIG. 13. By first expanding the center region of the stent S, the stent may be pulled from the collars, facilitating deployment within the blood vessel BV, as shown in FIG. 14. With certain stent designs, such as the Palmaz-Schatz stent described above, axial foreshortening of the stent will contribute to its release.

An alternative construction, similar to the embodiment of FIGS. 12-14, is illustrated in FIG. 15. The delivery catheter 12 includes a pair of spaced-apart collars 80 and 82, generally the same as described above. Instead of employing axial retention rings 84 and 86, however, the catheter 12 employs a recess or cavity 88 which receives the stent S therein. The ends of the recess 88 serve as abutments for maintaining axial placement of the stent S prior to expansion.

Figure 15A:
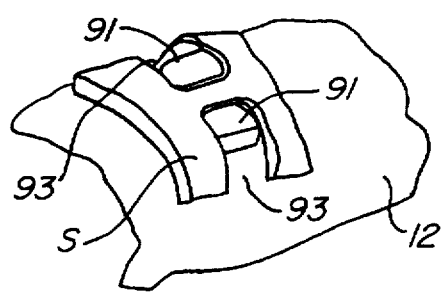
FIGS. 15A–15C illustrate still further prosthesis retaining structures which may be employed in the delivery catheters of the present invention.
Figure 15B:
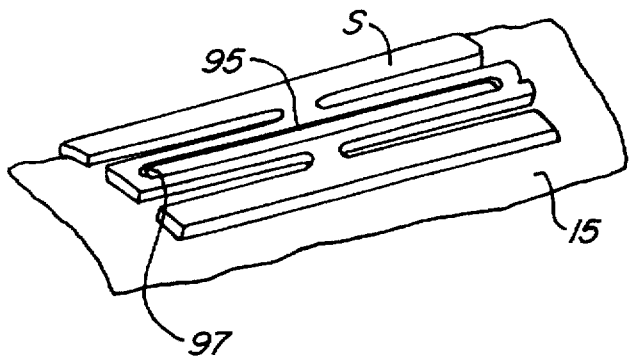

Referring to FIGS. 15A and 15B, the use of protrusions as retaining structure on catheter body 12 will be described. In FIG. 15A, A pair of protrusions or "bumps" 91 are formed on the exterior surface of the catheter body 12 and engage gaps 93 in a conventional stent S structure. In FIG. 15B, a single elongate protrusion 95 is illustrated which is received in a corresponding gap 97 in a conventional stent S structure, such as a Palmaz-Schatz stent.

Figure 15C:
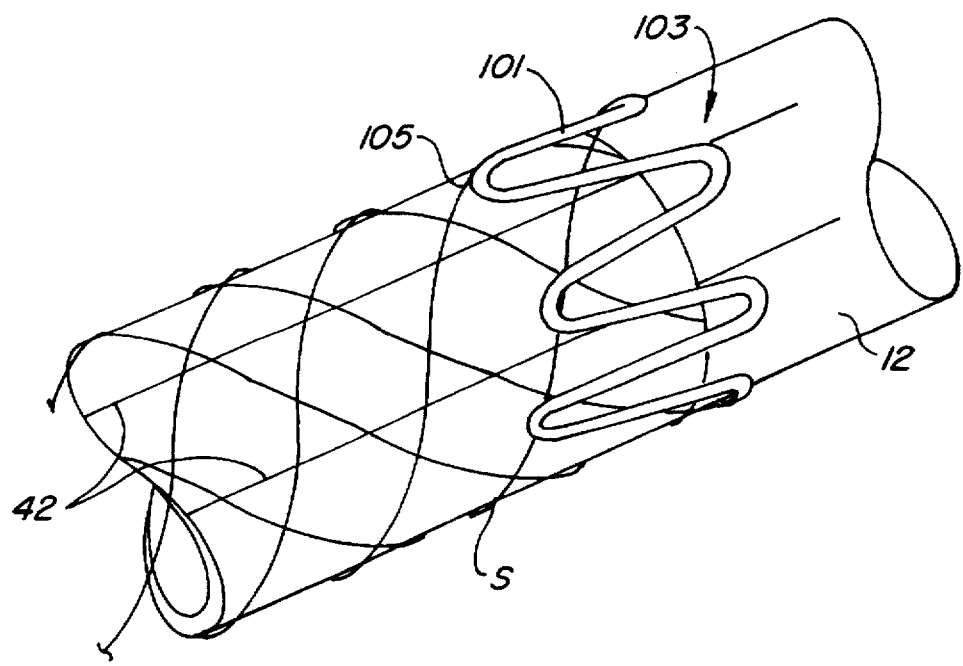

Referring now to FIG. 15C, an alternative collar-type retention structure on catheter body 12 is illustrated a serpentine ring 101 is attached at a first end 103 to the catheter body. The serpentine ring 101 is formed from a resilient material, such as a superelastic alloy, such as nitinol. An unattached or "free" end of the serpentine ring 101 extends over an end of the stent S to hold that end in place, as with similar collar structures in the previous embodiments. When the tubular body 12 is expanded, it will be appreciated that the serpentine ring will shorten so that the free end 105 moves away from the stent S, thus releasing the stent.

Yet another embodiment of the retaining structure of the present invention is illustrated in FIG. 16. There, a particular stent structure, which is described in detail in copending application Ser. No. 08/463,166, filed on Jun. 5, 1995, the full disclosure of which is incorporated herein by reference, is illustrated. The stent S' includes a plurality of end loops 90, each of which is held in place by a pair of straps 92. The straps 92 may extend over points on the periphery of the loop (as shown on the left side of FIG. 16) or may extend over adjacent points on two loops (as shown on the right hand side of FIG. 16). As illustrated in FIGS. 17A and 17B, the straps 92 are initially deployed over an axial split 42 so that, upon expansion, the strap 92 will split in half, as illustrated in FIG. 17B. The strap 92, for example, may be weakened in its middle to facilitate splitting, as shown in FIG. 17B. Alternatively, the attachment of either end of the strap 92 can be sufficiently weak to permit detachment upon expansion of the tubular catheter body 12.

Figure 18A:
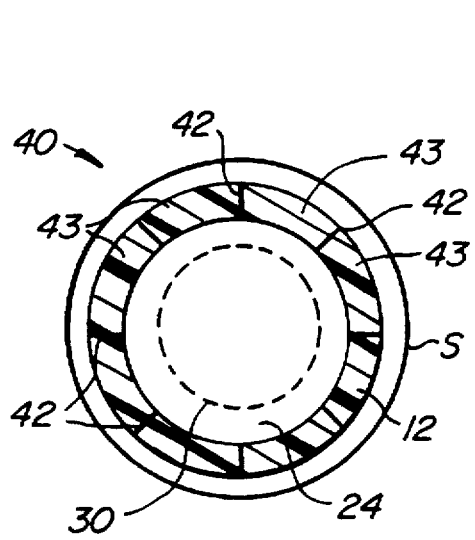
FIGS. 18A and 18B illustrate radial expansion of an axially split catheter body configuration.
Figure 18B:
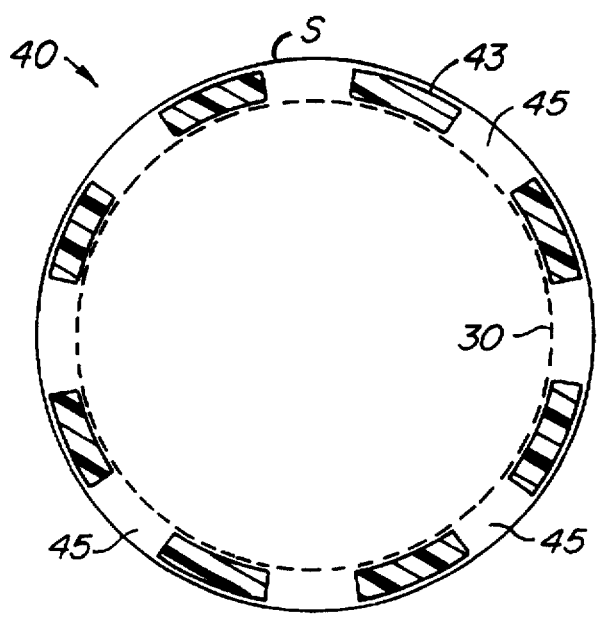

Referring now to FIGS. 18A and 18B, a first embodiment of the expansible region 40 of the tubular catheter body 12 is shown in cross-section. The expansible region 40 comprises the tubular catheter body, typically a single extrusion, optionally reinforced by axial members disposed therein (not illustrated). The tubular body 12 is split along a plurality of axial lines 42 creating a corresponding plurality of axial segments 43 therebetween. The balloon 30 is shown in lumen 24 in its uninflated configuration in FIG. 18A. Inflation of balloon 30, shown in broken line in FIG. 18B, causes the axial segments 43 to expand radially outward and to move circumferentially apart, leaving gaps 45 therebetween. Expansion of the segments 43, in turn, causes radial expansion of the stent S which circumscribes the elements. Other forms of splitting patterns are also possible. Such forms are described in copending application Ser. No. 08/241,428, filed on May 11, 1994, assigned to the assignee of the present application, the full disclosure of which is incorporated herein by reference.

Figure 19A:
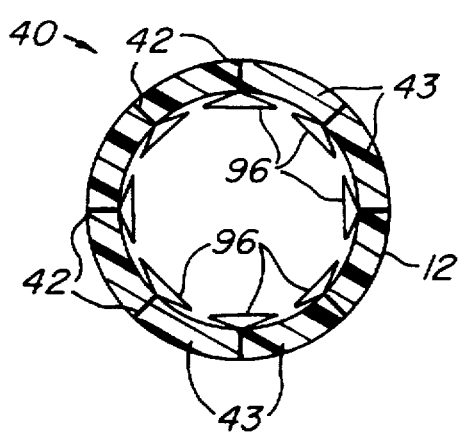
FIGS. 19A and 19B illustrate radial expansion of an axially split catheter body having web elements between adjacent axial segments.
Figure 19B:
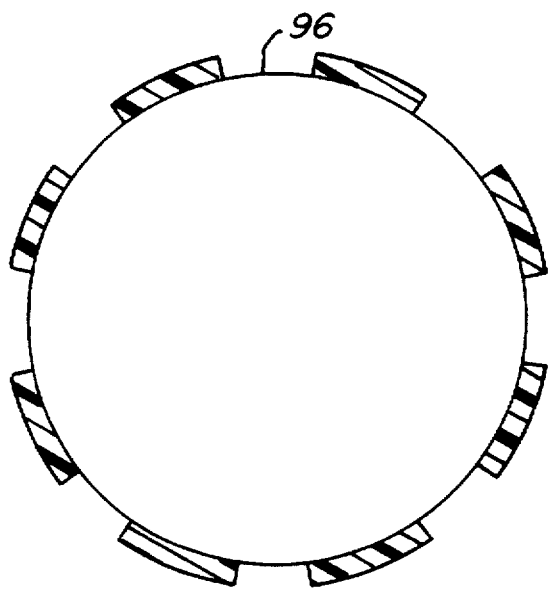

Optionally, the radially expansible portion 40 may include a plurality of web portions 96 which are formed between adjacent axial segments 43. The web portions 96 will initially be folded typically over the inner lumen of the tubular body 12, as shown in FIG. 19A. Upon balloon expansion as shown in FIG. 19B, the web portions 96 will bridge the gaps 45 which existed in the embodiment of FIGS. 18A and 18B. The webs 96 may be formed of elastomeric material, permitting the expansible portion 40 to conform tightly to the internal balloon up to and including its full inflation. Alternatively, the web portions 96 may be formed from a non-distensible material in order, optionally, limit balloon inflation.

Figure 20:
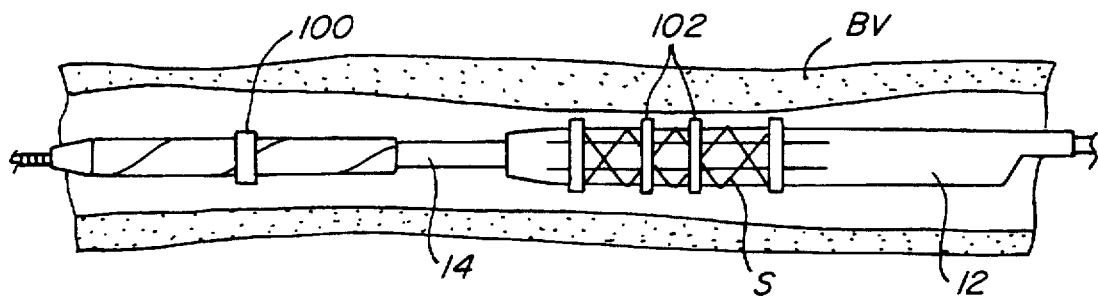
FIGS. 20–22 illustrate positioning of a prosthesis delivery catheter over a balloon catheter using specially positioned fluoroscopic markers.
Figure 21:
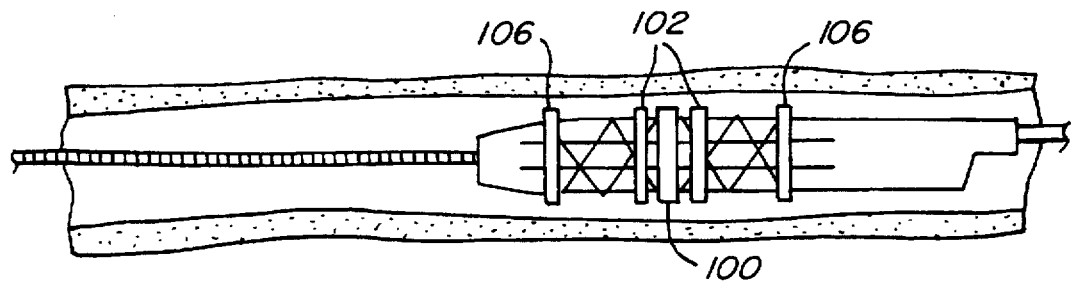
Figure 22:
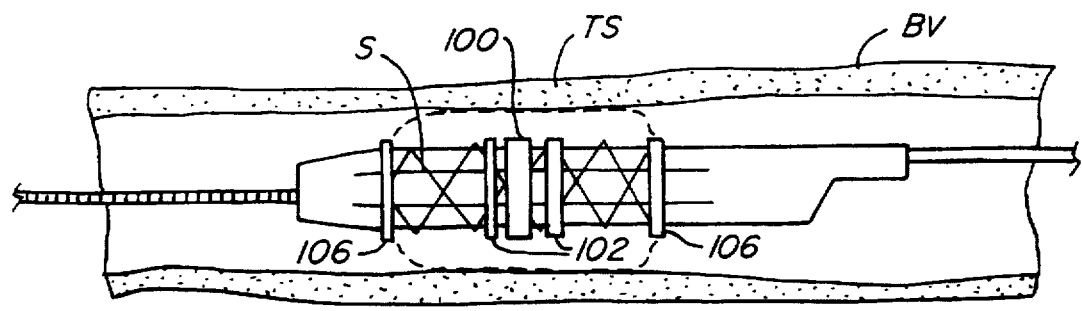

Referring now to FIGS. 20-22, a particular marker system for fluoroscopically delivering a stent S in a blood vessel BV as illustrated. Conventional balloon catheters, such as catheter 14, typically include at least a single fluoroscopic marker 100 located near the center of the balloon. The delivery catheter 12 of the present invention will include at least one and preferably a pair of markers 102 located at or near the center of the expansible portion 40, so that the delivery catheter marker(s) may be aligned over the balloon catheter marker 100, as illustrated in FIG. 21. The catheter 12 and/or stent S will also include markers 106 at the proximal and distal ends of the stent S. These markers will be useful for aligning the stent S at the target site TS in the blood vessel BV, as illustrated in FIG. 22. Markers 100 and 106 are preferably composed of Pebax 72D loaded with tungsten, as described above. Thus, the delivery method of the present invention comprises observing the treatment site under fluoroscopic imaging. A fluoroscopic marker on the tubular catheter body carrying the stent S is first aligned properly over a marker on the balloon angioplasty catheter, as shown in FIG. 21. The pair of axially spaced-apart fluoroscopic markers at opposite ends of the stent S (which markers may be present on the stent S itself or on the delivery catheter) are then aligned at the target site TS in a desired manner by repositioning, if necessary, the angioplasty catheter and stent delivery catheter simultaneously. The stent S may then be delivered by balloon expansion, as shown in FIG. 22.

Figure 23:
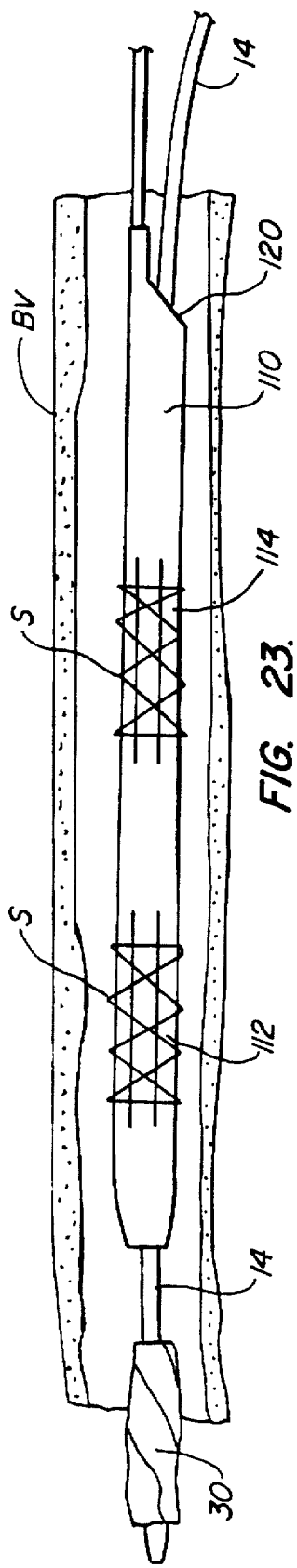
FIGS. 23–25 illustrate use of a prosthesis delivery catheter which carries a pair of prosthesis thereon.
Figure 24:
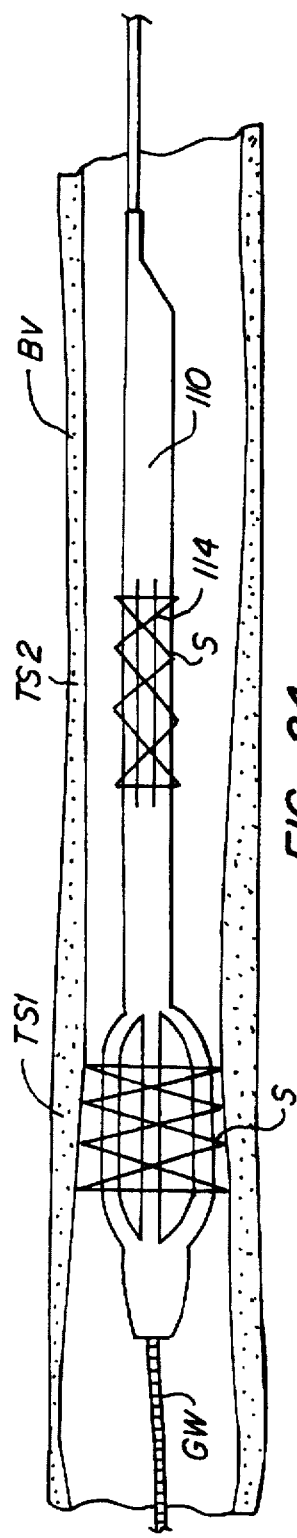
Figure 25:
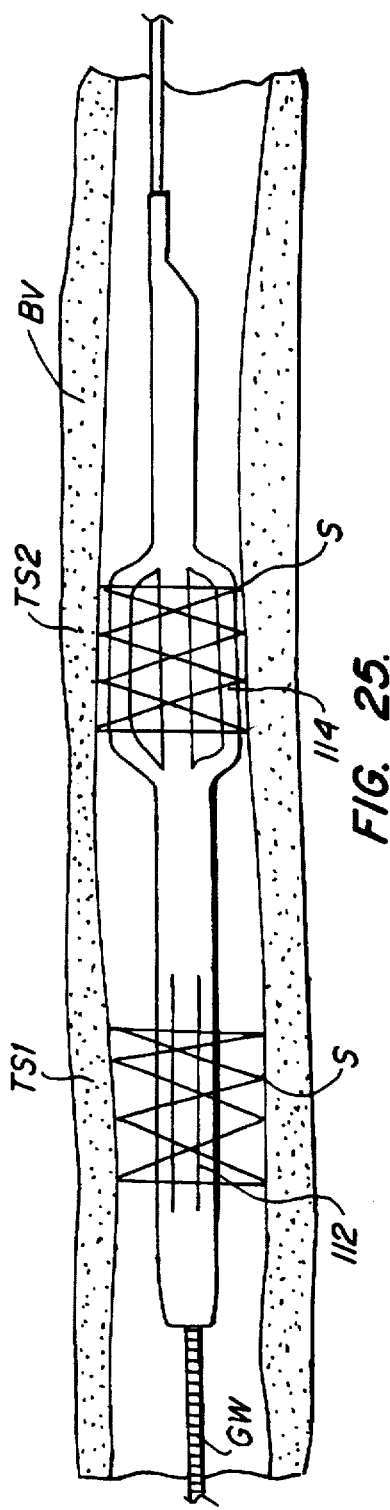

Delivery of a pair of stents S within a blood vessel BV using a delivery catheter 110 having a first expansible region 112 and a second expansible region 114 is illustrated in FIGS. 23-25. The catheter 110 is mounted over the balloon catheter 14 by introducing the balloon catheter through the proximal port 120, generally is described above for the other embodiments of the delivery catheter. The distalmost stent S is then positioned at a first target site TS1 and the balloon 30 inflated therein to expand the stent S, as shown in FIG. 24. After the balloon 30 is deflated, the proximal stent S may then be positioned at a second target site TS2 and the balloon 30 inflated therein to deploy the stent S as shown in FIG. 25. In FIGS. 23-25, the stents S are shown to be deployed near each other without substantial movement of the delivery catheter 112 between deployments. It will be appreciated that the delivery catheter 110 and balloon catheter 30 can be moved to other locations in the same or a different artery prior to deployment of the proximal stent S. Less desirably, the proximal stent S could be deployed first, with the distal stent S being deployed at a different location.

Figure 26:
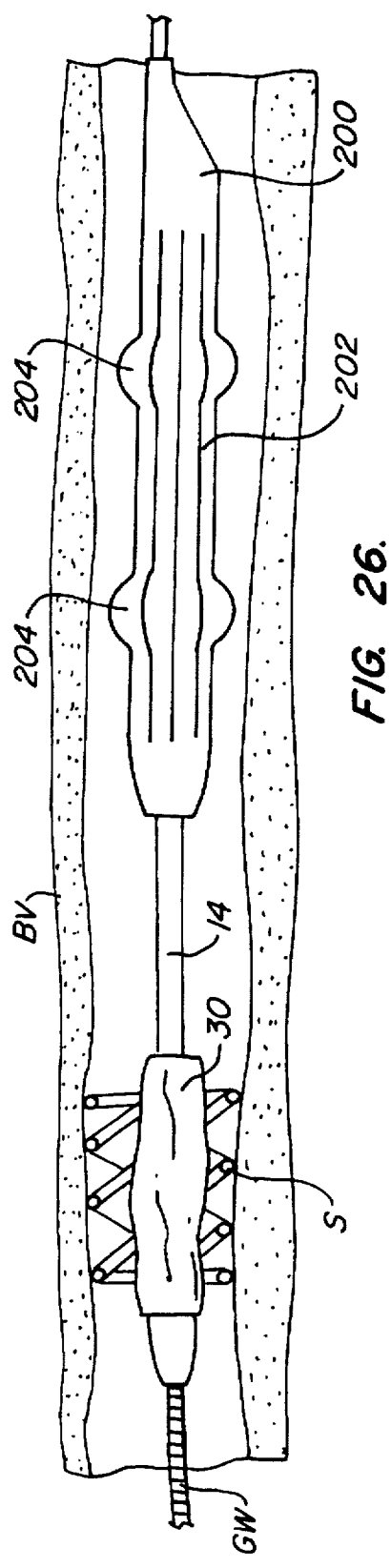
FIGS. 26–27 illustrate use of a special tubular catheter for anchoring the ends of a previously deployed stent in a tubular body lumen.
Figure 27:
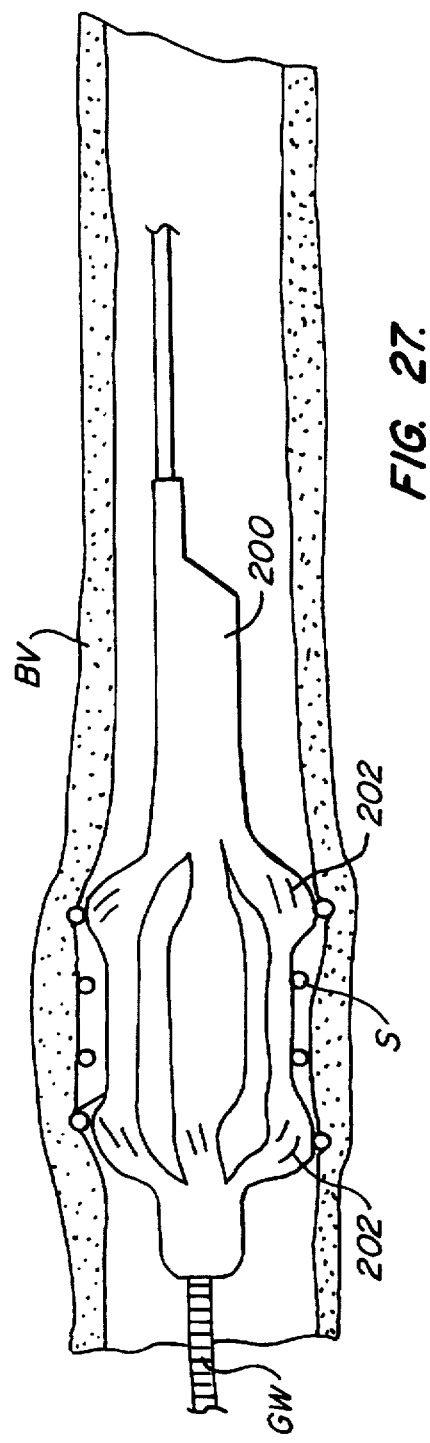
Figure 28:
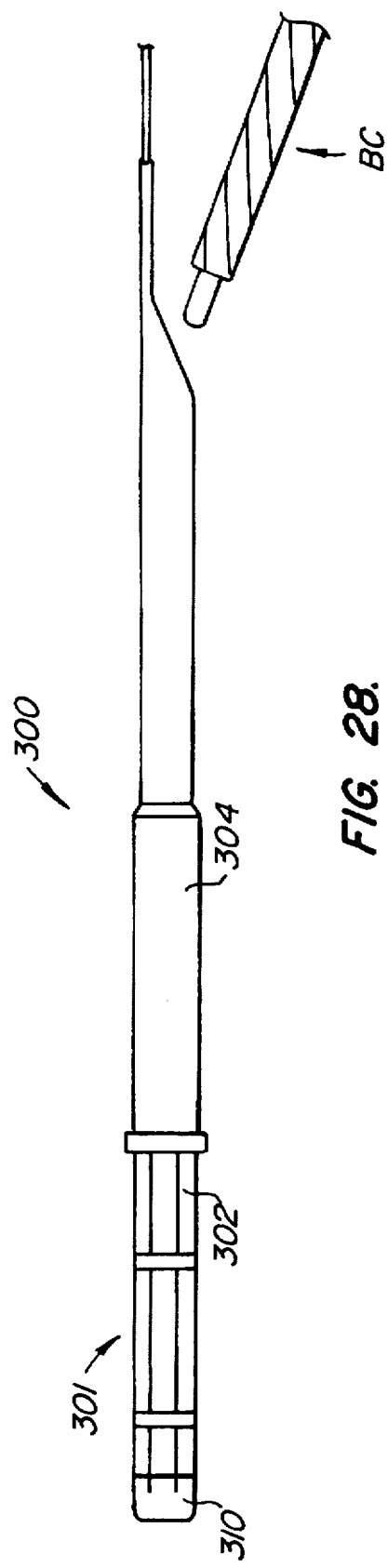
FIGS. 28–33 illustrate use of the catheter of FIGS. 9A–9H for delivering a stent according to the method of the present invention.

Referring now to FIGS. 26 and 27, yet another aspect of the method of the present invention will be described. A tubular catheter body 200 comprises a radially expansible portion 202 having a pair of axially spaced-apart circumferential protrusions 204 thereon. Balloon catheter 14 may be used to deploy a stent S in a conventional manner, as shown in FIG. 26. Tubular catheter body 200 may then be advanced over the balloon so that protrusions 204 align with opposite ends of the stent S using fluoroscopic markers (not shown). By then expanding the balloon 30, the protrusions 204 can be engaged against the opposite ends of the stent S, to further expand and anchor the ends into the wall of the blood vessel BV. While it is preferred that the tubular catheter body 200 include a pair of axially spaced-apart protrusions 204, it will be appreciated that a similar catheter structure having only a single protrusion could be utilized by deploying the balloon therein two times, i.e., once at each end of the stents.

Figure 29:
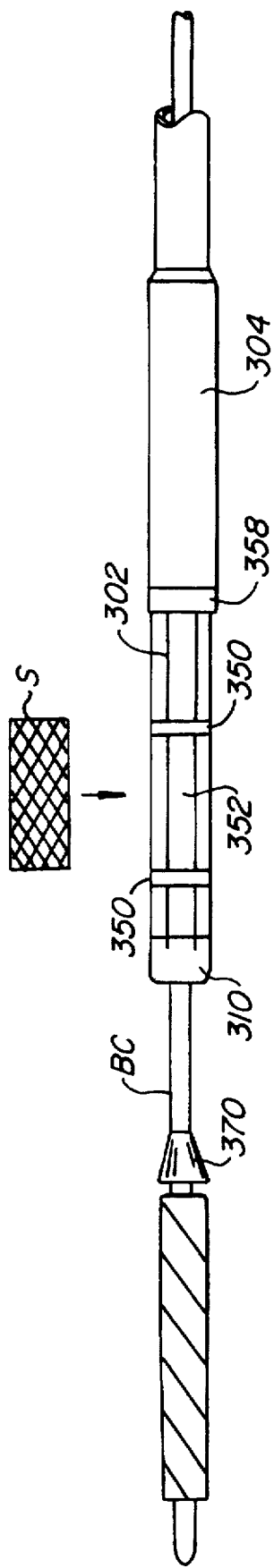
Figure 30:
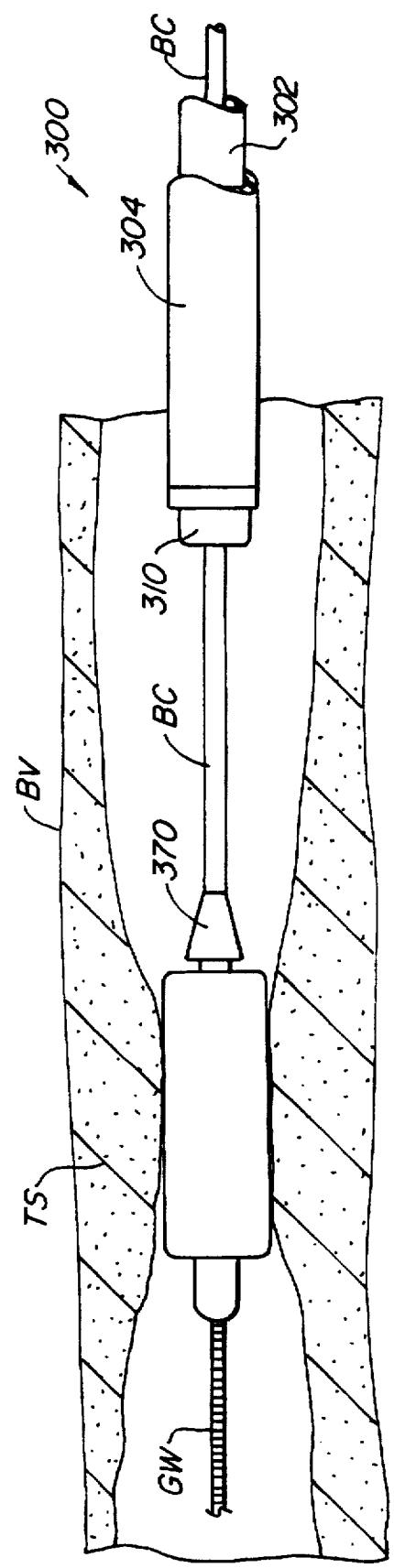

Referring now to FIGS. 28-33, delivery of a stent S using the catheter system 300 of FIGS. 9A-9H will be described. The catheter 301 is loaded onto a balloon catheter BC prior to mounting the stent S onto the expansible short sleeve 302. The interior lumen of the distal-most portion of the short sleeve 302 where the stent S is mounted will be sized slightly smaller than the balloon of the balloon catheter BC so that passage of the balloon will cause some radial dilation of the sleeve 302. For that reason, the stent is not mounted onto the delivery catheter 301 until after loading onto the balloon catheter BC. As illustrated in FIG. 29, after the balloon of balloon catheter BC has passed through the distal end 310 of the delivery catheter, the stent S is mounted onto the receptacle region 352 between the radiopaque markers 350, as illustrated. The stent S, of course, will not be loaded from the side (as shown) but rather will be passed coaxially first over the balloon catheter BC and then over one end of the catheter 301 and will then be crimped into the receptacle region 352 in a conventional manner. The balloon catheter BC is provided with a conical expansion element 370, for reasons that will be described below. The sheath 304 is then advanced distally so that it covers stent S, and the balloon catheter BC and stent delivery catheter 301 are introduced to a target site TS within a blood vessel BV, as illustrated in FIG. 30. The balloon of balloon catheter BC is then inflated to treat the target site TS in a conventional manner, typically over a guidewire GW.

Figure 31:
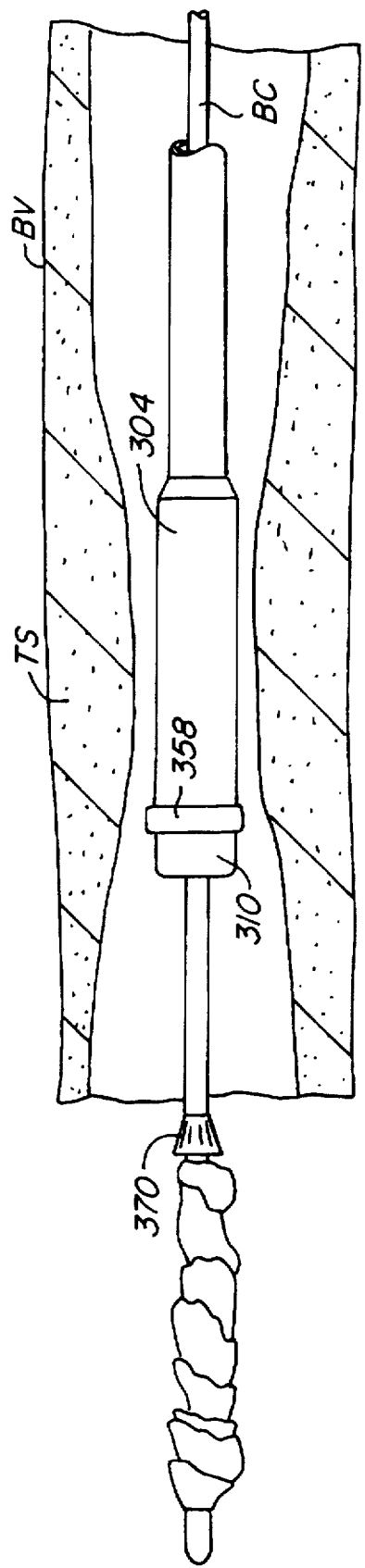
Figure 32:
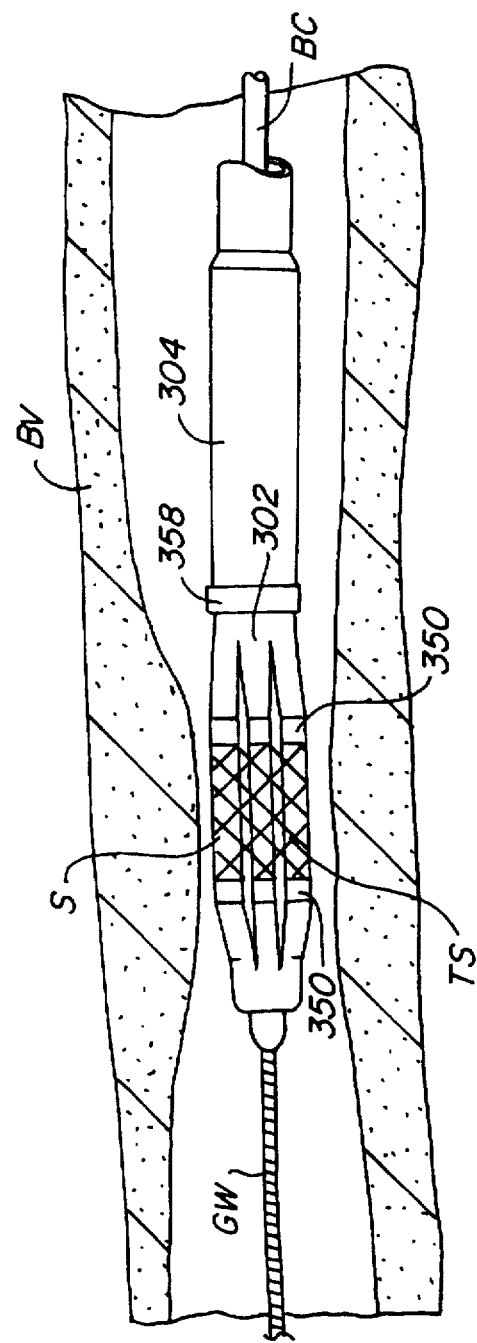

After the balloon of balloon catheter BC is deflated, the balloon catheter BC and the assembly of the catheter 301 and sheath 304 will be advanced. The deflated balloon lies distally beyond the target site TS and the sheath 304 lies within the target site TS as shown in FIG. 31. The sheath 304 will then be retracted using handle 320, while the stent S is maintained within the target site TS. Full retraction of the sheath 304 can be confirmed by fluoroscopically observing the marker 358 pass over markers 350 on either side of the stent S. The balloon is next retracted proximally so that the conical element 370 begins to enter the expansible tip 310 of the delivery catheter 301. As the balloon of balloon catheter BC is drawn proximally into the sleeve 302, the conical element 370 will cause predilation of the stent S to accommodate the deflated balloon, as shown in FIG. 32. It will be appreciated that the deflated and partially refolded balloon will not be as compact as the balloon prior to its initial expansion. Thus, the lumen of sleeve 302 is smaller than the refolded balloon in order to reduce the distal profile of catheter system 300 as much as possible. Partial expansion of the stent S is shown in FIG. 32.

Figure 33:
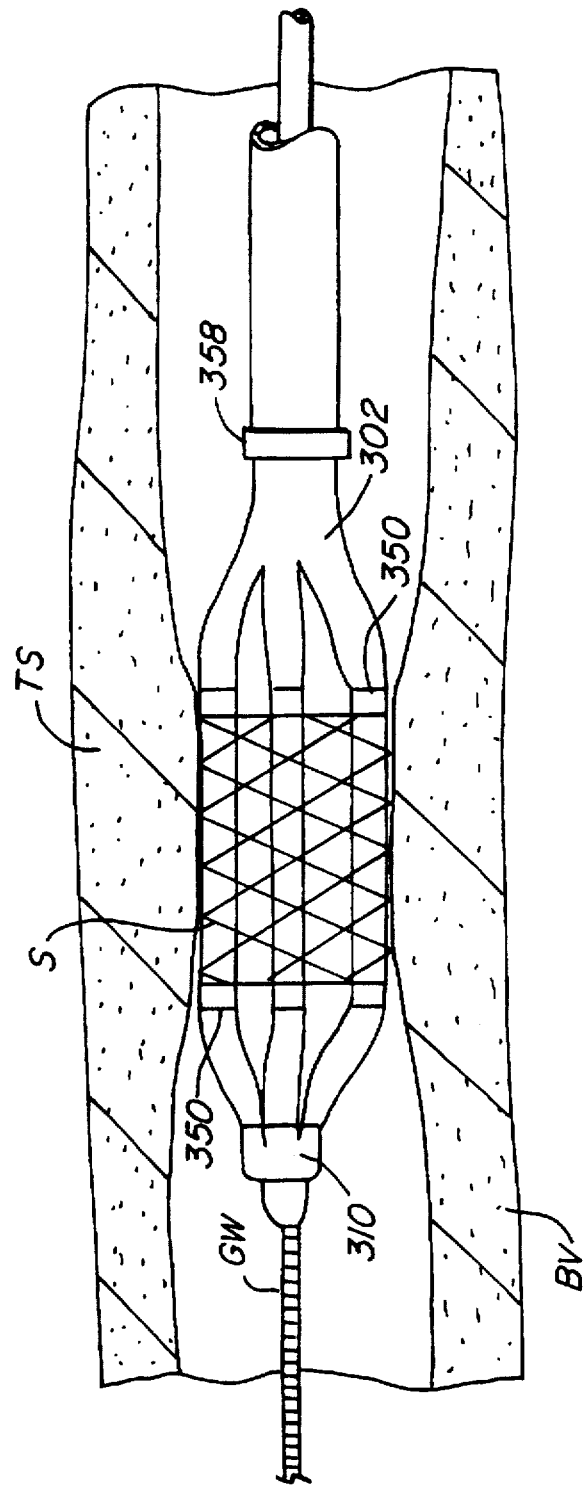

After the balloon of balloon catheter BC is in place, it can be inflated in order to expand the stent S against the inner lumenal wall in the region of target site TS as shown in FIG. 33. After the stent is fully deployed, the balloon of balloon catheter BC may be deflated, and both catheters withdrawn over the guidewire GW in a conventional manner.

While particularly suitable for the method of FIGS. 28–33, the catheter of FIGS. 9A–9H can also be used with the earlier described methods where the stent is not predilated.

Referring now to FIGS. 34–36, an alternative expansible structure which may be employed in any of the catheters of the present invention will be described. Heretofore, the expansible portion of the sleeve of the delivery catheter has generally consisted of a flexible polymeric tube section which is axially split in order to allow radial expansion. Instead of an axially split polymeric tube, an expansible region 400 of a delivery catheter 402 may comprise a plurality flexible, usually metal struts 404, as shown in FIGS. 34 and 35. As shown in those figures, a total of five peripherally spaced-apart struts are provided. This number is not critical, and as few as three and as many as nine struts may conveniently be employed. The struts 404 may be ribbons, round wires, or have a variety of other cross-sectional shapes. The struts will have to be attached to the proximal and distal portions 408 and 410, respectively, of the catheter 402 in a secure manner, typically using adhesives, heat bonding, or the like. In the exemplary embodiment, the struts 404 will be stainless steel ribbon having a thickness in the range from 0.001 to 0.002 inches and a width in the circumferential direction in the range from 0.01 to 0.03 inches. Radiopaque markers 414 may be provided immediately proximal and distal to a stent receiving region 416 defined therebetween.

The use of straight struts 404, shown in FIGS. 34 and 35, can sometime result in buckling when the catheter is tracked across a tight radius. Such buckling can be avoided through the use of struts 420 (FIG. 36) which can axially extend and retract when the catheter is tracked around a curved vessel. For example, the struts 420 can incorporate a serpentine pattern which permits both axial elongation on the outer radius of a curve and shortening on the inner radius of curve as a result of bending of the catheter.

Although the foregoing invention has been described in some detail by way of illustration and example, for purposes of clarity of understanding, it will be obvious that certain changes and modifications may be practiced within the scope of the appended claims.

What is claimed is:

1. A catheter for use in combination with a balloon catheter for delivering a radially expansible tubular prosthesis having transverse surfaces, said catheter comprising:

a tubular catheter body having a proximal end, a distal end, and a lumen therebetween, wherein the catheter body is axially split over a distal region thereof to define a radially expansible portion, and wherein the lumen slidably receives the balloon catheter so that a balloon thereon can be aligned within the radially expansible portion of the body; and a structure comprising abutting surfaces attached to the axially split region of the catheter body which is adapted to engage the transverse surfaces on the tubular prosthesis to inhibit axial movement thereof.

2. A catheter as in claim 1, wherein the catheter body has a length from 5 cm to 40 cm and the radially expansible portion has a length from 2.5 cm to 4.5 cm.

3. A catheter as in claim 1, further comprising a proximal shaft attached to the proximal end of the tubular catheter body.

4. A catheter as in claim 3, wherein the tubular catheter body has a length in the range from 5 cm to 40 cm, the radially expansible portion has a length from 2.5 cm to 4.5 cm, and the proximal shaft has a length from 90 cm to 150 cm.

5. A catheter as in claim 1, wherein the structure further comprises a sheath which is slidable between a first position covering the radially expansible portion including the abutting surfaces and a second position proximal of the radially expansible portion.

6. A catheter as in claim 5, wherein the sheath has an inner surface which includes a shoulder which engages a proximal surface on the tubular catheter body to limit distal movement of the sheath relative to the body.

7. A catheter as in claim 1, wherein the structure further comprises an everted sheath which is drawn from a first position covering at least a portion of the radially expansible portion to a second position proximal of the radially expansible portion.

8. A catheter as in claim 1, wherein the structure further comprises at least one axial member which is slidable between a first position over the expansible portion and a second position proximal of the radially expansible portion.

9. A catheter as in claim 8, wherein the structure comprises a plurality of axial members which are translatable between a first position over the expansible portion and a second position proximal of the radially expansible portion.

10. A catheter as in claim 1, wherein the structure further comprises a proximal collar which extends over the proximal end of the prosthesis and a distal collar which extends over the distal end of the prosthesis.

11. A catheter as in claim 10, wherein the collars are elastomeric and arranged to constrain expansion of the proximal and distal ends of the balloon so that the balloon expands first over a central portion thereof, wherein such expansion pulls the ends of the prosthesis from the collars.

12. A catheter as in claim 1, wherein the abutting surfaces are disposed at proximal and distal ends of the radially expansible portion of the catheter body.

13. A catheter as in claim 1, wherein the abutting surfaces are defined by protrusions formed on the axially split region of the catheter body and aligned to lie within at least one gap inside the prosthesis when the prosthesis is on the catheter.

14. A catheter as in claim 13, wherein at least one pair of protrusions is positioned to engage circumferentially spaced-apart gaps on the prosthesis.

15. A catheter as in claim 13, wherein at least one axially elongate protrusion is positioned to engage a similar gap in the prosthesis.

16. A catheter as in claim 1, wherein the abutting surfaces are defined by spaced-apart rings disposed on the axially split region of the catheter body.

17. A catheter as in claim 1, wherein the axially split region comprises a plurality of axial segments having webs therebetween.

18. A catheter as in claim 17, wherein the webs are elastomeric.

19. A catheter as in claim 17, wherein the webs are non-compliant.

20. A catheter as in claim 1, wherein the structure comprises a pair of axially spaced-apart radiopaque rings secured to the outside of the catheter body within the axially split region, wherein the rings are axially split to permit expansion with the expandable portion of the body.

21. A catheter system comprising:

a catheter as in claim 1, and a radially expansible tubular prosthesis disposed over the radially expansible portion of the tubular catheter body of the catheter.

22. A catheter system as in claim 21, wherein the prosthesis is plastically deformable and disposed on the catheter body in a collapsed configuration.

23. A catheter system as in claim 22, further comprising a sterile package containing the catheter having the tubular prosthesis mounted thereover.

* * * * *